US006825180B2

(12) United States Patent
McKennon et al.

(10) Patent No.: US 6,825,180 B2
(45) Date of Patent: Nov. 30, 2004

(54) PYRIDOPYRIMIDINE COMPOUNDS AND THEIR USES

(75) Inventors: Marc J. McKennon, Bellevue, WA (US); J. Peter Klein, Vashon, WA (US); Michael Coon, Seattle, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 162 days.

(21) Appl. No.: 09/859,503

(22) Filed: May 18, 2001

(65) Prior Publication Data

US 2004/0023995 A1 Feb. 5, 2004

(51) Int. Cl.$^7$ .................... C07D 471/04; A61K 31/519; A61P 11/06; A61P 19/02; A61P 17/06
(52) U.S. Cl. ........................ 514/81; 544/244; 544/279; 514/264.1
(58) Field of Search ........................... 544/279; 514/258

(56) References Cited

U.S. PATENT DOCUMENTS

| | | | |
|---|---|---|---|
| 3,235,554 A | | 2/1966 | Papesch |
| 4,515,795 A | | 5/1985 | Hinze et al. |
| 4,808,587 A | * | 2/1989 | Go et al. ..................... 514/258 |
| 4,880,810 A | | 11/1989 | Lowe, III |
| 5,039,666 A | | 8/1991 | Novick |
| 5,264,437 A | | 11/1993 | Wilhelm et al. |
| 5,556,854 A | | 9/1996 | Furrer et al. |
| 5,629,423 A | | 5/1997 | Klein et al. |
| 5,648,357 A | | 7/1997 | Bianco et al. |
| 5,734,051 A | | 3/1998 | Spicer et al. |
| 5,801,182 A | | 9/1998 | Klein et al. |
| 5,849,780 A | * | 12/1998 | Di Malta et al. ............ 514/409 |
| 6,075,029 A | | 6/2000 | Klein et al. |

FOREIGN PATENT DOCUMENTS

| | | |
|---|---|---|
| EP | 0 608 565 | 8/1994 |
| EP | 0 696 590 | 2/1996 |
| EP | 0 994 113 | 4/2000 |
| GB | 1 401 549 | 11/1989 |
| WO | WO94/22449 | 10/1994 |
| WO | WO94/22863 | 10/1994 |
| WO | WO94/24133 | 10/1994 |
| WO | WO95/20589 | 8/1995 |
| WO | WO95/22546 | 8/1995 |

OTHER PUBLICATIONS

Cytokines, http://home.attbi.com/~bkrentzman/misc/how.things.work/dna.transcription/cytokines.html.*
Chemokines, Horst Ibelgaufts' COPE:Cytokines Online Pathfinder Encyclopaedia, http://www.copewithcytokines.de/cope.cgi?001668.*
National Psoriasis Foundation "New & Notices" http://www.psoriasis.org/enbrel.approval.jan02.htm.*
"Centocor Places Congestive Heart Failure Clinical Program On Hold" http://www.jnj.com/news_finance/402.htm.*
Hackh's CHemical Dictionary, 3$^{rd}$ Edition p. 106.*
Merriam Webster 9$^{th}$ New Collegiate Dictionary p. 79 and 346 and 937.*
Morrison and Boyd, "Organic Chemistry" 6$^{th}$ edition p. 754.*
CRC Handbook, 75$^{th}$ Edition, p. 2–24 (1994).*
Hawley's Condensed Chemical Dicitionary, 1997, p. 1099.*
"Organic Chemistry", 6$^{th}$ Edition (Morrison & Boyd) 1992, apges 250–258.*
Trinchieri, Giorgio, Interleukin–12: A Cytokine Produced by Antigen–Presenting Cells with Immunoregulatory Functions in the Generations of T–Helper Cell Type 1 and Cytotoxic Lymphocytes, *Blood* 84: 4008–4027 (1994).
Kennedy, Mary, et al., "Interleukin–12 Regulates the Proliferation of Th1, but not Th2 or Th0, Clones", *Eur. J. Immunol.*, 24:2271–2278, 1994.
Morris, S.C. et al., "Effects of IL–12 on in Vivo Cytokine Gene Expression and Ig Isotype Selection", *J. Immunol*, 152:1047 (1994).
McKnight, A.J., et al., "Effects of IL–12 on Helper T Cell–Dependent Immune Responses in Vivo", *J. Immunol*, 152:2172 (1994).
Hotamisligil and Spiegelman, Tumor Necrosis Factor α: A Key Component of the Obesity–Diabetes Link, *Diabetes*, 43:1271–1278,(1994a).
Hotamisligil et al., "Increased Adipose Tissue Expression of Tumor Necrosis Factor–α in Human Obesity and Insulin Resistance", *J. Clin. Invest*, 95:2409–2415(1995).
Hotamisligil et al., "Reduced Tyrosine Chinese Activity of the Insulin Receptor in Obesity–Diabetes", *J. Clin Invest*, 94:1543–1549(1994b).
Coon, Michael, et al., "Selective Pharmacologic Inhibition of Murine and Human IL–12–Dependent TH1 Differentiation and IL–12 Signaling", J. Immuno, 163:6567–6574(1999).
"Generation of Interleukin 4(IL–4)–producing Cells In Vivo and In Vitro: IL–2 and IL–4 Required for In Vitro Generation of IL–4–producing Cells", by Le Gros, et al., The Journal of Experimental Medicine, vol. 172, Sep. 1990, pp. 921–929.
"Inhibition of Human Interleukin–12 Production by Pentoxifylline", by Moller et al., Immunology, vol. 91, 1997, pp. 197–203.
"The Immunology of Multiple Sclerosis and its Animal Model, Experimental Allergic Encephalomyelitis", by Owens et al., Neurologic Clinics, vol. 13, No. 1, Feb. 1995.
"Interleukin 12", R& D Systems Catalog, pp. 67–69, 1995.

(List continued on next page.)

*Primary Examiner*—Mark L. Berch
(74) *Attorney, Agent, or Firm*—Nixon & Vanderhye P.C.

(57) ABSTRACT

Novel pyridopyrimidine-based compounds are found to be useful for the treatment or prevention of symptoms or manifestations associated with diseases or disorders affected by cytokine intracellular signaling.

27 Claims, No Drawings

OTHER PUBLICATIONS

"Long-term Treatment of Chronic Relapsing Experimental Allergic Encephalomyelitis by Transforming Growth Factor–β2", by Racke et al., Journal of Neuroimmunology, vol. 46, 1993, pp. 175–184.

"Phosphodiesterase Inhibitor Pentoxifylline, a Selective Suppressor of T Helper Type 1—but not Type 2—associated Lymphokine Production, Prevents Induction of Experimental Autoimmune Encephalomyelitis in Lewis Rats", by Rott et al., Eur. J. Immumol., vol. 23, 1993, pp. 1745–1751.

"The Role of IL–12 in the Induction of Organ–Specific Autoimmune Diseases", by Trembleau et al., Immunology Today, vol. 16, No. 8, 1995, pp. 383–386.

Remington Pharmaceutical Sciences, Chapters 83–92, 1990, pp. 1519–1751.

"Development of $T_h1$ CD4 T Cells Through IL–12 Produced by *Listeria*–Induced Macrophages", by Hsieh et al., Science, vol. 260, Apr. 23, 1993, pp. 547–549.

"Natural Killer Cell Stimulatory Factor (Interleukin 12 [IL–12]) Induces T Helper Type 1 (Th1)–specific Immune Responses and Inhibits the Developement of IL–4–producing Th Cells", by Manetti et al., Journal of Exp. Medicine, vol. 177, Apr. 1993, pp. 1199–1204.

"Identification and Purification of Natural Killer Cell Stimulatory Factor (NKSF), A Cytokine with Multiple Biologic Effects on Human Lymphocytes", by Kobayashi et al., Journal of Exp. Medicine, vol. 170, Sep. 1989, pp. 827–846.

"Interleukin 12: A Key Modulator of Immune Function", by Wolf et al., Stem Cells, vol. 12, 1994, pp. 154–168.

"Interleukin–12: A Proinflammatory Cytokine with Immunoregulatory Functions that Bridge Innate Resistance and Antigen–Specific Adaptive Immunity", by Trinchieri, Annu. Rev. Immunol., vol. 13, 1995, pp. 251–276.

"The Role of Cytokines in Various Animal Models of Inflammation", by Heremans et al., Lymphokine Research, vol. 8, No. 3, 1989, pp. 329–333.

"Inducible Cell Contact Signals Regulate Early Activation Gene Expression During B–T Lymphocyte Collaboration", by Klaus et al., The Journal of Immunology, vol. 49, No. 6, Sep. 1992, pp. 1867–1875.

Anderson, G.L. et al. "Pyridopyrimidines. 6. Nucleophilic Substitutions in the Pyrido U2, 3–Dpyrimidine Series" Journal of Organic Chemistry, American Chemical Society, Easton, US, vol. 42, No. 6, 1977, pp. 993–996.

* cited by examiner

PYRIDOPYRIMIDINE COMPOUNDS AND THEIR USES

FIELD OF THE INVENTION

The present invention generally relates to novel pyridopyrimidine-based compounds, pharmaceutical compositions containing such compounds, methods for preparing such compounds and methods for using these compounds, alone or in combination with other therapeutic agents, for the treatment or prevention of symptoms or manifestations associated with diseases or disorders affected by cytokine intracellular signaling.

BACKGROUND OF THE INVENTION

Cellular signals necessary for cell growth, differentiation, response to bioregulatory molecules, infectious agents and physiological stress involve various biochemical processes. The ability to respond appropriately to such signaling events challenge the survival of the cell and ultimately the organism. Perturbations in the normal regulation of these specific responses can result in pathogenic events which lead to acute and chronic disease.

For example, inflammatory responses are a component of the pathogenesis of many vertebrate disorders/diseases, including those in humans. In its broadest meaning, the term "inflammation" denotes local as well as systemic responses, increased blood flow, vasodilation, fluid transudation from the vessels, infiltration of the tissues by leukocytes and, in some severe cases, intravascular thrombosis, damage to the blood vessels and extravasation of blood characterize local inflammation. The systemic inflammatory response, also denoted as an acute phase response, is characterized by various reactions including, for example, fever, leukocytosis and release of acute phase reactants into the serum. In severe cases, shock and death may occur. See Heremans et al., *Lymphokine Research* 8(3): 329–333 (1989). Diseases involving inflammation are particularly harmful when they afflict the respiratory system, resulting in obstructed breathing, hypoxemia, hypercapnia and lung tissue damage. Obstructive diseases of the airways are characterized by airflow limitation (i.e., airflow obstruction or narrowing) due to constriction of airway smooth muscle, edema and hypersecretion of mucous leading to increased work in breathing, dyspnea, hypoxemia and hypercapnia. While the mechanical properties of the lungs during obstructed breathing are shared between different types of obstructive airway diseases, the pathophysiology can differ. The inflammatory response is believed to be controlled by a variety of cellular events characterized by the influx of certain cell types and mediators, the presence of which can lead to tissue damage and sometimes death. Cytokines are believed to be primary factors in the biochemical cascade of events that regulate inflammatory responses.

Cytokines are a class of secreted, soluble proteins produced by a variety of cells in response to many different kinds of inducing stimuli, including environmental, mechanical, and pathological stresses. Lymphoid, inflammatory and hemopoietic cells secrete a variety of cytokines that regulate the immune response by controlling cell proliferation, differentiation and effector functions. For example, regulatory cytokines produced in response to T cell stimulation during an immune response can be immunosuppressive or immunostimulatory. The immune response and acute phase response associated with altered cytokine levels can occur, for example, due to disuse deconditioning, organ damage such as that associated with transplantation, cancer treatment, septic shock and other bacterially related pathologies, adverse drug reactions, nitric oxide mediated tissue damage and diabetes. Some cytokines induce or release other known mediators of inflammation. These systems are controlled by related feedback mechanisms. Thus, it is believed that inflammatory responses are not a result of a single cytokine being released in large quantities, but rather to a set of cytokines collectively acting via a network of intercellular signals to incite the inflammatory response.

Cytokines are well known in the art and include, but are not limited to, the tumor necrosis factors (TNFs), colony stimulating factors (CSFs), interferons (INFs), interleukins (IL-1, IL-2, IL-3, IL-4, IL-5, IL-6, IL-7, IL-8, IL-9, IL-10, IL-11, IL-12, IL-13, IL-14, and IL-15), transforming growth factors (TGFs), oncostatin M (OSM), leukemia inhibiting factor (LIF), platelet activating factor (PAF) and other soluble immunoregulatory peptides that mediate host defense responses, cell regulation and cell differentiation. See, e.g., Kuby, *Immunology* 2d ed. (W. H. Freeman and Co. 1994). Cytokines are normally present in very low concentrations in a tissue and their effects are mediated through binding to high affinity receptors on specific cell types. Various cytokines such as the interleukins (IL), interferons (IFN), colony stimulating factors (CSF) and tumor necrosis factors (TNF) are produced during immune, inflammatory, repair and acute phase responses and they control various aspects of these responses. Following induction of such an immune, inflammatory, repair or acute phase response, the concentrations of various cytokines can increase or decrease at different times. For example, increased levels of cytokines are associated with a variety of situations such as space flight, immobilization, spinal cord injury, and bed rest, which result in disuse deconditioning. During space flight, for example, TNF, IL-6, and IL-2 levels increase upon a subject's initial exposure to weightlessness and again upon return from space. Altered levels of cytokines have also been linked to abnormal bone metabolism and the rapid decalcification that occurs during immobilization, spinal cord injury, or long-term bed rest. Similarly, cytokine levels are altered during chronic states such as during repair and autoimmune reactions to organ damage, nephrotoxicity associated with the administration of cyclosporine to transplant subjects, cancer chemotherapy, as well as in individuals that are obese or suffering from diabetes, septic (endotoxic) shock or glomerulonephritis.

Cytokines, including the TNFs, CSFs, interferons and interleukins mediate host defense responses, cell regulation and cell differentiation. For example, these cytokines can induce fever in a subject, can cause activation of T cells, B cells and macrophages, and can even affect the levels of other cytokines, which result in a cascade effect whereby other cytokines mediate the biological levels and actions of the first cytokine.

Cytokines may regulate the immune response through immunostimulatory or immunosuppresive effects. For example, IL-10 can block activation of many of the inflammatory cytokines including TNF, IL-1 and IL-6, while upregulating anti-inflammatory cytokines, such as IL-4. IL-10, which is produced by macrophages and other cell types, also stimulates the proliferation of mast cells and thymocytes and inhibits various functions of monocytes and macrophages. As a consequence of this monocyte and macrophage inhibition, the activity of T cells is also affected. The full scope of the role of IL-10 in the immune system is only beginning to be understood.

Cytokines have multiple biological activities and interact with more than one cell type. Thus, it has not been possible to target one particular cytokine or cell type to prevent the damaging side effects of treatment. A better approach for preventing damage due to the unwanted and uncontrolled over-suppression or over-stimulation of cytokine activity would be to regulate the expression of the relevant or controlling cytokine or cytokines involved in an immune response without eliminating or over-expressing any one cytokine. Such a treatment would not create or aggravate a pathological or ongoing immune response. In this way, pathological immune-mediated effects, such as immunosuppression or autoimmune reactions, can be prevented and homeostasis can be maintained.

Corticosteroids have been used to modulate cytokine expression. However, they can cause complete immunosuppression and have other undesirable side effects, such as inducing "wasting" syndrome, diabetes and osteoporosis. For example, steroid therapy is a common treatment for MS because it is believed that steroids alter the trafficking of cells into the brain or reduce the secretion of cytokines by inflammatory cells in areas of inflammation. Although their effect in reversing some of the acute symptoms of autoimmune disease, such as MS, are well known, their side effects have precluded long-term use. Similarly, non-steroidal anti-inflammatory drugs (NSAID), are effective in treating inflammation and pain. However, NSAIDs also cause undesirable side effects by inhibiting prostaglandin production, which can lead to potentially severe complications including gastric ulceration, bleeding and renal failure.

One particular cytokine, IL-12, also referred to as natural killer cell stimulatory factor ("NKSF") or cytotoxic lymphocyte maturation factor ("CLMF"), is a potent immunoregulatory molecule that plays a role in a wide range of diseases. In particular, IL-12 is a heterodimeric cytokine that is produced by phagocytic cells, e.g., monocytes/macrophages, B-cells and other antigen-presenting cells ("APC") and is believed to act as a proinflammatory cytokine. It has several effects including 1) enhanced proliferation of T cells and NK cells, 2) increased cytolytic activities of T cells, NK cells, and macrophages, 3) induction of IFN-.gamma. production and to a lesser extent, TNF-α and GM-CSF, and 4) activation of TH1 cells. See Trinchieri, G., et al., *Blood*, 84:4008–4027 (1994). IL-12 has been shown to be an important costimulator of proliferation in Th1 clones (Kennedy et al., *Eur. J. Immunol.*, 24:2271–2278, 1994) and leads to increased production of IgG2a antibodies in serum (Morris, S. C., et al., *J. Immunol.*, 152:1047 (1994). Administration of IL-12 also decreases production of IgG1 antibodies (Morris, S. C., et al., *J. Immunol.*, 152:1047 (1994); McKnight, A. J., *J. Immunol.* 152:2172 (1994)), indicating suppression of the Th2 response. It is also believed that IL-12 plays a specific role in diseases exhibiting an inflammatory component, namely, diseases that exhibit cell-mediated inflammatory responses, such as, multiple sclerosis, diabetes, chronic inflammatory bowel disease, etc.

IL-12 affects both natural killer cells ("NK cells") and T-lymphocytes ("T cells"), and stimulates IFN-γ production by both of these cell types. For example, in NK cells, IL-12 stimulates: NK cell proliferation, membrane surface antigen up-regulation, LAK cell generation and NK cell activity elevation; induces IFN-γ and TNF-α production and the growth and expansion of either resting or activated NK cells; and increases soluble p55 and soluble p75 TNF receptor production and NK cell cytotoxicity. See *R&D Systems Catalog*, pp. 67–69 (1995). T cells recognize antigens via interaction of a heterodimeric (alpha/beta, or gamma/delta) receptor with short peptide antigenic determinants that are associated with major histocompatibility complex ("MHC") molecules. Mature T cells can be divided broadly into two functional categories by the presence of two mutually exclusive antigens on their cell surface, CD4 (helper) and CD8 (cytotoxic). The CD4 and CD8 antigens regulate T cell interactions with MHC and their mutually exclusive expression derives from their strict specificity for MHC. Class II MHC-restricted T cells are primarily CD4+ (a.k.a. "helper cells") and class I MHC-restricted T cells are CD8+ (a.k.a. "cytotoxic cells"). Mature T cells may be further distinguished by their effector phenotypes, e.g., pro-/anti-inflammatory or suppressor cells.

As mentioned above, IL-12 also affects T cells, including stimulation of T cell IFN-γ production in response to antigen. While CD8+ T cells are associated with cytotoxicity functions, CD4+ T cells are associated with helper function and secrete various cytokines that regulate and modulate immune responses. CD4+ T cells can be further subdivided into T helper 1 (Th1) and T helper 2 (Th2) subsets, according to the profile of cytokines they secrete. Therefore, Th1 cells produce predominantly inflammatory cytokines, including IL-2, TNF-α and IFN-γ, while Th2 cells produce anti-inflammatory cytokines such as IL-4, IL-5, IL-10, and IL-13 that are linked to B cell growth and differentiation.

The Th1 and Th2 CD4+ T cell subsets are derived from a common progenitor cell, termed Th0 cells. During an initial encounter with an antigen, the differentiation into Th1 and Th2 is controlled by the opposing actions of two key cytokines, namely IL-12 and IL4, which induce the differentiation of Th0 into Th1 and Th2, respectively. The development of Th1 and Th2 cells is primarily influenced by the cytokine milieu during the initial phase of the immune response, in which IL-12 and IL-4, respectively, play decisive roles. The cytokines produced by each Th-cell phenotype are inhibitory for the opposing phenotype. For example, Th1 cytokines enhance cell-mediated immunities and inhibit humoral immunity. Th2 cytokines enhance humoral immunity and inhibit cell-mediated immunities. See Trembleau et. al., *Immunology Today* 16(8): 383–386 (1995).

Some human disorders/diseases that arise from effects of the immune system are mediated by anti-inflammatory responses, including atopy. This T cell mediated immune response is called anti-inflammatory because the cytokines released by anti-inflammaotry effector T cells, IL-4 and IL-10 act to suppress the development of inflammatory responses. Atopy is a genetically determined state of hypersensitivity to environmental allergens. Type-1 allergic reactions are associated with the IgE antibody production, eosinophilia and a group of diseases including, without limitation, asthma, hay fever, and atopic dermatitis. Anti-inflammatory responses also arise from infection with extracellular pathogens, like bacteria and worms. Anti-inflammatory responses are mediated by differentiated T cells and are called T2 responses. T2 (both Th2 and Tc2) responses are initiated by the release of the cytokine IL-4 from activated T and B cells and they direct and control B cell responses to infection. T2 responses also stimulate the release of IgE, histamines and other allergic effector molecules.

Furthermore, CD4+ Th1 cells play a role in the pathogenesis of immunological disorders. These cells primarily secrete cytokines associated with inflammation such as IFN-γ, TNF-α, TNF-β and IL-2. IFN-γ is an important component of the inflammatory response and resultant pathology of those diseases exhibiting an inflammatory response. Heremans, et al. In addition to its role in inflammatory response, IFN-γ also contributes to phagocytic cell activation (i.e., macrophage activation), and up-regulation of MHC expression on the surface of antigen-presenting cells ("APC") and other cells. Further, this cytokine is implicated generally in inflammatory immune responses, and in autoimmune diseases, such as multiple sclerosis ("MS"), specifically. See Owens et al., *Neurologic Clinics*, 13(1):51–73 (1995). Furthermore, steroid treatment broadly attenuates cytokine production, but it cannot modulate it selectively, e.g., just the Th0, the Th1 or the Th2 pathways.

IL-12 also plays a role in the induction of Th1-cell-mediated autoimmunity. Research evidence points to a critical role for IL-12 in the pathogenesis of rodent models of Th1-mediated autoimmune diseases such as type-1 diabetes, multiple sclerosis, rheumatoid arthritis, inflammatory bowel disease, and acute graft-versus-host disease. Thus, Th1 cells are believed to be involved in the induction of experimental autoimmune diseases, as demonstrated in adoptive transfer experiments demonstrating the CD4+ cells producing Th1-type lymphokines can transfer disease, as shown in models of experimental autoimmune disease, such as experimental allergic encephalomyelitis ("EAE") (also known as experimental allergic encephalitis) and insulin-dependent diabetes mellitus ("IDDM"). See Trinchieri, *Annu. Rev. Immunol.* 13(1):251–276 (1995). For instance, EAE is an inflammatory T cell mediated, paralytic, demyelinating, autoimmune disease that can be induced in a number of rodents as well as primates. Owens et al. One of the ways that EAE can be induced is by immunization of animals with myelin basic protein ("MBP"). Likewise, administration of IL-12 induces rapid onset of IDDM in 100% of NOD female mice. Thus, one goal of immunotherapy research and development efforts has been to limit inflammatory responses while leaving the specificity of the immune system, deemed necessary for host protection, intact.

Other treatments that target immune system components include lymphocyte cytotoxic drugs such as cyclophosphamide and azathioprine. These drugs act like "sledgehammers" in that they suppress the entire immune system and raise problems that attend broad-spectrum immunosuppression therapies. The same problems also are likely with newer therapies such as cyclosporine, anti-CD4 monoclonal antibodies, and others. Other treatments for IL-12 mediated diseases, including MS, can involve the administration of anti-IL-12 antagonists such as antibodies. Anti-IL-12 antibodies have been shown to inhibit the development of IDDM and EAE. See Trinichieri. However, antibody based immunotherapy may result in immune complex formation and deposition, thus leading to glomerulonephritis, vasculitis and arthritis.

Moreover, symptomatic treatment with beta-agonists, anticholinergic agents and methyl xanthines have been clinically beneficial for the relief of discomfort but fail to stop the underlying inflammatory processes that cause the disease. The frequently used systemic glucocorticosteroids have numerous side effects, including, but not limited to, weight gain, diabetes, hypertension, osteoporosis, cataracts, atherosclerosis, increased susceptibility to infection, increased lipids and cholesterol, and easy bruising. Aerosolized glucocorticosteroids have fewer side effects but can be less potent and have side effects, such as thrush.

The use of anti-inflammatory and symptomatic relief reagents is a serious problem because of their side effects or their failure to attack the underlying cause of an inflammatory response. Other anti-inflammatory agents, such as cromolyn and nedocromil are much less potent and have fewer side effects. Anti-inflammatory agents that are primarily used as immunosuppressive agents and anti-cancer agents (i.e., cytoxan, methotrexate and Immuran) have also been used to treat inflammation. These agents, however, have serious side effect potential, including, but not limited to, increased susceptibility to infection, liver toxicity, drug-induced lung disease, and bone marrow suppression. Such drugs have found limited clinical use, for example, in the treatment of most airway hyperresponsiveness lung diseases.

To prevent pathological conditions or disruption of normal immune mediated functions caused by the aberrant expression of cytokines as described above, it would be advantageous if cytokine levels could be manipulated and efficaciously controlled. Thus, a need exists for agents that can regulate the activity of cytokines in a subject without causing undesirable side effects. Furthermore, a need exists for identifying agents which can be used in the treatment of pathologies and conditions associated with altered cytokine levels. In particular, there remains a need for novel therapeutic compounds and methods that ameliorate or inhibit the deleterious effects of responses mediated by specific cytokines, such as, for example, IL-12 or IL-4, without adversely affecting the other components of the immune system that are deemed necessary for protecting the host and without the attendant disadvantages of conventionally available compounds and methods.

SUMMARY OF THE INVENTION

It is an object of the present invention to provide novel therapeutic compounds that are stable and/or metabolically stable, including pharmaceutical compositions thereof and methods useful for inhibiting cytokine signaling.

It is another object of the present invention to provide novel therapeutic compounds, pharmaceutical compositions thereof and methods that are capable of limiting the inflammatory or anti-inflammatory response of a subject without adversely affecting the specificity of the immune system deemed necessary for protecting the subject.

It is a further object of the present invention to provide novel therapeutic compounds, pharmaceutical compositions thereof and methods that are capable of treating or preventing disease or conditions such as asthma or diabetes (IDDM and NIDDM).

The above and other objects are accomplished by a compound, including pharmaceutically acceptable derivatives (e.g., racemic mixtures, resolved enantiomers, diastereomers, tautomers, salts and solvates thereof) or prodrugs thereof, having the following formula:

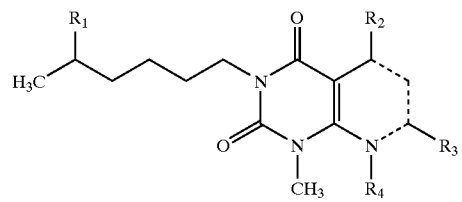

wherein:
the dashed lines, i.e., " - . - . - . ", represent either a single or double bond;

$R_1$ is selected from a member of the group consisting of hydrogen, hydroxyl, methoxyl, alkylaminoalkyl, N—OH, acylamino group, cyano group, sulfo, sulfonyl, sulfinyl, sulfhydryl (mercapto), sulfeno, sulfanilyl, sulfamyl, sulfamino, and phosphino, phosphinyl, phospho, phosphono and —$NR_aR_b$, wherein each of $R_a$ and $R_b$ may be the same or different and each is selected from the group consisting of hydrogen and optionally substituted: alkyl, cycloalkyl, alkenyl, cycloalkenyl, alkynyl, aryl, heteroaryl, and heterocyclic group.

$R_2$ and $R_3$ are independently selected from a member of the group consisting of halo, thio, OXO, $C_{(1-20)}$alkyl, $C_{(1-20)}$hydroxyalkyl, $C_{(1-20)}$thioalkyl, $C_{(1-20)}$alkylthio, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraminoalkyl, $C_{(1-20)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(1-20)}$alkoxyl, $C_{(1-20)}$alkoxyalkyl, and $C_{(1-20)}$dialkoxyalkyl.

$R_4$ may be hydrogen or an optionally substituted member of the group consisting of alkyl, cycloalkyl, alkenyl, cycloalkenyl, alkynyl, aryl, heteroaryl, and heterocyclic group.

The above novel compounds of the present invention act as, inter alia, cytokine regulatory agents to regulate the aberrant or altered expression of one or more cytokines that may occur in various conditions, including, for example, pathologies, immune responses and inflammatory responses. Such conditions are considered together for purposes of the present invention in that they are characterized, in part, by altered or aberrant cytokine activity and, therefore, are amenable to regulation by one or more cytokine regulatory agents. As used herein, the term "characterized by" means contributes or affects, at least in part. Although cytokine contribution can be, it does not have to be, the only, primary, or even a major factor or cause of a condition treatable by the compounds of the present invention. For example, it is well understood in the art that an infection has altered cytokine levels and is, therefore, a condition characterized by cytokine activity, but that cytokine activity is only a part of the infectious condition. As used herein, the term "condition characterized by altered or aberrant cytokine activity" includes all cytokine regulated or modulated pathologies and injuries, including the immune, inflamatory and healing processes associated with an injury. The skilled artisan can recognize such a condition by detecting an increased or decreased level of activity of a particular cytokine as compared to the normal level of the cytokine expected to be found in a healthy individual. Methods for determining such normal levels are well known in the art.

The present invention particularly provides novel therapeutic compounds having a pyridopyrimidine-based structural core and methods of using such tricylic compounds for affecting, preventing, treating, inter alia, the cellular responses associated with Th1 or Th2 cell-mediated diseases, without affecting the other components of the immune system that are deemed necessary for host protection. The compounds and methods of the present invention are particularly characterized by an ability to inhibit IL-12 or IL-4 signaling. Without wishing to be bound by theory, it is believed that the therapeutic compounds of the present invention short-circuit the inflammatory cascade by Th1, T2, Th2 or T2 cell development, emphasizing the present invention's importance in disease therapy by inhibiting cytokine signaling in the regulation of inflammatory or anti-inflammatory disorders. Specifically, the pyridopyrimidine-based compounds of the present invention may impede signaling that induces differentiation of T cells to Th1 or Th2 cells. For example, differentiated Th1 cells produce high levels of IFN-γ, which provokes inflammation, a component of many disease conditions that the inventive compounds and methods target. Moreover, the pyridopyrimidine-based compounds of the present invention act to ameliorate the insulin secretory defects found in Type-2 diabetes myelitis (NIDDM) that are believed to be associated with defects in fatty acid metabolism by affecting insulin secretion and glucose tolerance.

The present invention also achieves the above and other objects by, inter alia, providing novel therapeutic compounds and methods for treating or preventing disease conditions characterized by altered or aberrant cytokine activity. Examples of such disease conditions include, but are not limited to: (1) inflammatory diseases or disorders, such as, for example, arthritis, asthma, chronic inflammatory diseases, chronic intestinal inflammation, psoriasis, septic shock, septicemia, allergic contact dermatitis, ankylosing spondylitis and adult respiratory distress syndrome; (2) autoimmune diseases or disorders or other patho-immunogenic diseases or reactions, such as, for example, allergic reactions or anaphylaxis; allergic encephalomyelitis, amyotrophic lateral sclerosis, bullous pemphigold, Celiac disease, chronic active hepatitis, chronic thyroiditis, gastritis, Goodpastures syndrome, graft-versus-host disease (acute and/or chronic), glomerulonephritis; hemolytic anemia, immune thrombocytopenia purpura, inflammatory bowel disease (e.g., Crohn's Disease and ulcerative colitis), isopathic thrombocytopenic purpura, juvenile arthritis, lupus disorders (e.g., systemic lupus erythematosus), male infertility (autoimmune), multiple sclerosis, myasthenia gravis, neutropenia, pemphigus vulgaris, parasitic mediated immune dysfunctions (e.g. Chagas' Disease), pemphigus vulgaris, pernicious anemia, polyarteritis nodosa, primary antiphospholipid syndrome, primary biliary cirrhosis, primary Sjogren's syndrome, Reiter's disease, rheumatic fever, rheumatoid arthritis, sarcoidosis, scleroderma, thrombocytopenia, Sjorgens disease, sympathetic ophthalmia, thyroid diseases (e.g., Graves' and Hashimoto's disease), Type-1 (IDDM) and Type-2 (NIDDM) diabetes mellitus, uveitis, and viral myocarditis (Cocksakie B virus response); (3) neurodegenerative diseases such as, for example, Alzheimer's disease, Parkinson's disease, and primary lateral sclerosis; (4) chronic lymphocytic leukemia (CLL), hairy cell leukemia, prolymphocytic leukemia, well differentiated lymphocytic lymphomas, infectious mononucleosis, human immunodeficiency virus; (5) adverse reactions associated with cancer chemotherapy; (6) diseases such as atherosclerosis and diabetes that are believed to be mediated by free radicals and nitric oxide action; (7) bacterial endotoxic sepsis and related shock; (8) pain; (9) Type-1 hypersensitivity allergic reactions such as asthma, hay fever, eczema, urticaria, food allergy and atopic dermatitis; (10) cachexia; and (11) angiogenesis, including neoplasia; metastasis; etc. The methods of using the compounds of the present invention are particularly useful in the treatment of autoimmune diseases, MS, diabetes mellitus (Type-1 or -2) or asthma. The compounds of the present invention may be employed in any suitable conventional manner for the treatment of the above diseases. Such methods of treatment, their dosage levels and requirements may be selected by those of skill in the art from available methods and techniques that are further described below, that are known in the art or that are readily determinable using routine experimentation.

The present invention also includes a method for inhibiting a cellular process or an activity mediated by cytokine, the method comprising:

(a) contacting cytokine responsive cells with a compound as defined in claim 1; and (b) determining that the cellular process or activity mediated by the cytokine is inhibited;

wherein said activity is the secretion of a cytokine selected from the group consisting of tumor necrosis factor, colony stimulating factor, interferon, IL-1, IL-2, IL-3, IL-4, IL-5, IL-6, IL-7, IL-8, IL-9, IL-10, IL-11, IL-12, IL-13, IL-14, IL-15, transforming growth factor, oncostatin M, leukemia inhibiting factor, and platelet activating factor.

The present invention further includes a method for treating a T1 or T2 cell-mediated response in a mammal in need of such treatment, the method comprising: administering to the mammal a therapeutically effective amount of the compound of claim 1, wherein said compound is capable of inhibiting an IL-12 mediated cellular process or activity, thereby inhibiting the response.

Additional aspects, embodiments and advantages of the present invention will be set forth, in part, in the description that follows, or may be learned from practicing or using the present invention. The objects and advantages may be realized and attained by means of the features and combinations particularly pointed out throughout this written description and the appended claims. It is to be understood that the foregoing general description and the following detailed description are exemplary and explanatory only and are not to be viewed as being restrictive of the invention as claimed.

DETAILED DESCRIPTION OF PREFERRED EMBODIMENTS

All patents, patent applications and publications cited in this description are incorporated herein by reference in their entirety.

"Acyl," as used herein, denotes a radical provided by the residue after removal of hydroxyl from an organic acid. Examples of such acyl radicals include, without limitation, alkanoyl and aroyl radicals. Examples of lower alkanoyl radicals include, without limitation, formyl, acetyl, propionyl, butyryl, isobutyryl, valeryl, isovaleryl, pivaloyl, hexanoyl, trifluoroacetyl.

"Acylamino" denotes an N-substituted amide, i.e., RC(O)—NH and RC(O)—NR'—. A non-limiting example is acetamido.

"Acyloxy" means 1 to about 4 carbon atoms. Suitable examples include, without limitation, alkanoyloxyl, benzoyloxyl and the like.

"Alicyclic hydrocarbon" means an aliphatic radical in a ring with 3 to about 10 carbon atoms, and preferably from 3 to about 6 carbon atoms. Examples of suitable alicyclic radicals include, without limitation, cyclopropyl, cyclopropylenyl, cyclobutyl, cyclopentyl, cyclohexyl, 2-cyclohexen-1-ylenyl, cyclohexenyl and the like.

"Alkenyl" is intended to include hydrocarbon chains of either a straight or branched configuration and one or more unsaturated carbon-carbon bonds which may occur in any stable point along the chain. For example, alkenyl refers to an unsaturated acyclic hydrocarbon radical in so much as it contains at least one double bond. Such radicals contain from about 2 to about 40 carbon atoms, preferably from about 2 to about 10 carbon atoms and more preferably about 2 to about 6 carbon atoms. Non-limiting examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like "Alkoxyl" and "Alkyloxyl" embrace linear or branched oxy-containing radicals each having alkyl portions of one to about ten carbon atoms. Preferred alkoxyl radicals are "lower alkoxyl" radicals having one to six carbon atoms. Examples of such radicals include methoxyl, ethoxyl, propoxyl, butoxyl and tert-butoxyl.

"Alkoxyalkyl" embraces alkyl radicals having one or more alkoxyl radicals attached to the alkyl radical, that is, to form monoalkoxyalkyl and dialkoxyalkyl radicals. The "Alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include, without limitation, fluoromethoxy, chloromethoxy, trifluoromethoxy, trifluoromethoxy, fluoroethoxy and fluoropropoxy. Further, "Alkoxycarbonyl" means a radical containing an alkoxy radical, as defined herein, attached via an oxygen atom to a carbonyl radical. More preferred are "lower alkoxycarbonyl" radicals with alkyl portions having 1 to 6 carbons. Examples of such lower alkoxycarbonyl (ester) radicals include, without limitation, substituted or unsubstituted methoxycarbonyl, ethoxycarbonyl, propoxycarbonyl, butoxycarbonyl and hexyloxycarbonyl.

"Alkoxycarbonyl" means a radical containing an alkoxy radical, as defined herein, attached via an oxygen atom to a carbonyl radical. More preferred are "lower alkoxycarbonyl" radicals with alkyl portions having one to six carbons. Examples of such lower alkoxycarbonyl (ester) radicals include methoxycarbonyl, ethoxycarbonyl, propoxycarbonyl, butoxycarbonyl and hexyloxycarbonyl.

"Alkoxycarbonylalkylene" embraces alkylene radicals substituted with an alkoxycarbonyl radical as defined herein. More preferred are "lower alkoxycarbonylalkylene" radicals with alkylene portions having one to six carbons. Examples of such lower alkoxycarbonylalkylene radicals include substituted or unsubstituted methoxycarbonylmethyl, ethoxycarbonylmethyl, methoxycarbonylethyl and ethoxycarbonylethyl.

"Alkoxyl" represents an alkyl group of indicated number of carbon atoms attached through an oxygen bridge. "Alkoxy" and "Alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include, without limitation, methoxy, ethoxy, propoxy, butoxy and tert-butoxy.

"Alkyl" or "lower alkyl" is intended to include both branched and straight-chain saturated aliphatic hydrocarbon radicals/groups having the specified number of carbon atoms. In particular, "Alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. "Substituted alkyl" refers to an alkyl group as defined herein having from 1 to 5 substituents selected, without limitation, from the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxyl, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic group.

"Alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like.

"Alkylaminoalkyl" embraces radicals having one or more alkyl radicals attached to an aminoalkyl radical.

"Alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined herein.

"Alkylcarbonyl," "Arylcarbonyl" and "Aralkylcarbonyl" include radicals having alkyl, aryl and aralkyl radicals, as defined herein, attached via an oxygen atom to a carbonyl radical. Examples of such radicals include, without limitation, substituted or unsubstituted methylcarbonyl, ethylcarbonyl, phenylcarbonyl and benzylcarbonyl. "Alkylcarbonyl," includes radicals having alkyl radicals, as defined herein, attached to a carbonyl radical. Examples of such radicals include substituted or unsubstituted methylcarbonyl, ethylcarbonyl, propylcarbonyl, butylcarbonyl, and pentylcarbonyl.

"Alkylcarbonylamino" embraces amino groups which are substituted with an alkylcarbonyl radical. More preferred alkylcarbonylamino radicals are "lower alkylcarbonylamino" having lower alkylcarbonyl radicals as defined herein attached to amino radicals.

"Alkylene" refers to a diradical of a branched or unbranched saturated hydrocarbon chain, preferably having from 1 to 40 carbon atoms, more preferably 1 to 10 carbon atoms, even more preferably 1 to 6 carbon atoms. This term is exemplified by groups such as methylene (—CH$_2$—), ethylene (—CH$_2$CH$_2$—), the propylene isomers (e.g.— CH$_2$CH$_2$CH$_2$— and —CH(CH$_3$)CH$_2$—), and the like. "Substituted alkylene" refers to: (1) an alkylene group as defined herein having from 1 to 5 substituents selected from a member of the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxyl, oxyacylamino, azido, cyano, halogen, hydroxyl, keto, thioketo, carboxyl, carboxylalkyl, thiol, thioalkoxyl, substituted thioalkoxyl, aryl, aryloxyl, thioaryloxyl, heteroaryl, heteroaryloxyl, thioheteroaryloxyl, heterocyclic, heterocyclooxyl, thioheterocyclooxyl, nitro, and —NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include, without limitation, those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group; (2) an alkylene group as defined herein that is interrupted by 1-20 atoms independently chosen from oxygen, sulfur and NR$_a$, where R$_a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or (3) an alkylene group as defined herein that has both from 1 to 5 substituents as defined herein and is also interrupted by 1 to 20 atoms as defined herein. Examples of substituted alkylenes are chloromethylene (—CH(C$_1$)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxdy-2-(2-ethoxy-ethoxy)ethane (—CH$_2$CH$_2$O—CH$_2$CH$_2$—OCH$_2$CH$_2$—OCH$_2$CH$_2$—), and the like.

"Alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl.

"Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include, without limitation, methylsulfonyl, ethylsulonyl and propylsulfonyl. The "Alkylsulfonyl" radicals may be further substituted with one or more halo atoms, such as fluoro, chloro or bromo, to provide haloalkylsulfonyl radicals.

"Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "Alkylsulfonyl" radicals may be further substituted with one or more halo atoms, such as fluoro, chloro or bromo, to provide haloalkylsulfonyl radicals.

"Alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

"Alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

"Alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include, without limitation, methylthiomethyl.

"Alkylthioalkylene" embraces radicals containing an alkylthio radical attached through the divalent sulfur atom to an alkyl radical of one to about ten carbon atoms. More preferred alkylthioalkylene radicals are "lower alkylthioalkylene" radicals having alkyl radicals of one to six carbon atoms. Examples of such lower alkylthioalkylene radicals include methylthiomethyl.

"Alkynyl" is intended to include hydrocarbon chains of either a straight or branched configuration and one or more triple carbon-carbon bonds which may occur in any stable point along the chain, such as ethynyl, propynyl and the like. For example, alkynyl refers to an unsaturated acyclic hydrocarbon radical in so much as it contains one or more triple bonds, such radicals containing about 2 to about 40 carbon atoms, preferably having from about 2 to about 10 carbon atoms and more preferably having 2 to about 6 carbon atoms. Non-limiting examples of suitable alkynyl radicals include, ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

"Alkoxyalkyl" embraces alkyl radicals having one or more alkoxy radicals attached to the alkyl radical to form, for example, monoalkoxyalkyl and dialkoxyalkyl radicals. The "Alkoxy" radicals may be further substituted with one or more halo atoms, such as fluoro, chloro or bromo, to provide "Haloalkoxy" radicals.

"Aminoalkyl" embraces alkyl radicals substituted with amino radicals. More preferred are "lower aminoalkyl" radicals. Examples of such radicals include, without limitation, aminomethyl, aminoethyl, and the like.

"Aminocarbonyl" denotes an amide group of the formula —C(=O)NH$_2$.

"Aralkoxy" embraces aralkyl radicals attached through an oxygen atom to other radicals.

"Aralkoxyalkyl" embraces aralkoxy radicals attached through an oxygen atom to an alkyl radical.

"Aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. Preferred are "lower aralkyl" radicals having branched or unbranched lower alkyl portions containing one to six carbon atoms. Examples include benzyl, diphenylmethyl, triphenylmethyl, phenylethyl, and diphenylethyl. The aryl in said aralkyl may be additionally substituted with halo, alkyl, alkoxy, haloalkyl and haloalkoxy.

"Aralkylamino" embraces aralkyl radicals attached through an nitrogen atom to other radicals.

"Aralkylthio" embraces aralkyl radicals attached to a sulfur atom.

"Aralkylthioalkyl" embraces aralkylthio radicals attached through a sulfur atom to an alkyl radical.

"Aromatic hydrocarbon radical" means 4 to about 16 carbon atoms, preferably 6 to about 12 carbon atoms, more preferably 6 to about 10 carbon atoms. Examples of suitable aromatic hydrocarbon radicals include, without limitation, phenyl, naphthyl, and the like.

"Aroyl" embraces aryl radicals with a carbonyl radical as defined herein. Examples of aroyl include, without limitation, benzoyl, naphthoyl, and the like and the aryl in said aroyl may be additionally substituted.

"Aryl" refers to an unsaturated aromatic carbocyclic group of from 5 to 20 carbon atoms having a single ring (e.g., phenyl) or multiple condensed (fused) rings (e.g., naphthyl or anthryl). "Aryl" embraces aromatic radicals such as phenyl, naphthyl, tetrahydronaphthyl, indane and biphenyl. Unless otherwise constrained by the definition for the aryl substituent, such aryl groups can optionally be substituted with from 1 to 5 substituents selected from a member of the group consisting of acyloxyl, hydroxyl, thiol, acyl, alkyl, alkoxyl, alkenyl, alkynyl, cycloalkyl, cycloalkenyl, substituted alkyl, substituted alkoxyl, substituted alkenyl, substituted alkynyl, substituted cycloalkyl, substituted cycloalkenyl, aminoacyl, acylamino, alkaryl, aryl, aryloxyl, azido, carboxyl, carboxylalkyl, cyano, halo, nitro, heteroaryl, heteroaryloxyl, heterocyclic, heterocyclooxyl, aminoacyloxyl, oxyacylamino, thioalkoxyl, substituted thioalkoxyl, thioaryloxyl, thioheteroaryloxyl, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include, without limitation, limitation, alkyl, alkoxyl, halo, cyano, nitro, trihalomethyl, and thioalkoxy (i.e., —S-alkyl). More preferred aryl comprise 6–12 membered aryl. Examples of such radicals include, but are not limited to, acyl, alkenoxy, alkenyl, alkenylamino, alkoxy, alkoxyalkyl, alkoxycarbonyl, alkoxycarbonylalkyl, alkyl, alkylamino, alkylaminoalkyl, alkylcarbonyl, alkylcarbonylamino, alkylsulfinyl, alkylsulfonyl, alkylthio, alkynoxy, alkynyl, alkynylamino, amino, aminoalkyl, aminocarbonyl, aminocarbonylalkyl, aralkoxy, aralkoxycarbonyl. aryl, arylamino, arylcarbonyl, arylcarbonylamino, aryloxy, aryloxycarbonyl, arylsulfinyl, arylsulfonyl, arylthio, biphenyl. carboxy, carboxyalkyl, cyano, formyl, halo, haloalkyl, haloalkylsulfinyl, haloalkylsulfonyl, heterocyclyl, heterocyclylamino, heterocyclylcarbonyl, heterocyclyloxycarbonyl, heterocyclyloxyl, hydroxyalkyl, hydroxyl, indane naphthyl, nitro, nitroalkyl, phenyl, and tetrahydronaphthyl. Aryl moieties may also be substituted at any substitutable position with one or more substituents. Suitable non-limiting examples of such substituents include acyl, alkenoxy, alkenyl, alkenylamino, alkoxy, alkoxyalkyl, alkoxycarbonyl, alkoxycarbonylalkyl, alkyl, alkylamino, alkylaminoalkyl, alkylcarbonyl, alkylcarbonylamino, alkylsulfinyl, alkylsulfonyl, alkylthio, alkynoxy, alkynyl, alkynylamino, amino, aminoalkyl, aminocarbonyl, aminocarbonylalkyl, aralkoxy, aralkoxycarbonyl, aryl, arylamino, arylcarbonyl, arylcarbonylamino, aryloxy, aryloxycarbonyl, arylsulfinyl, arylsulfonyl, arylthio, carboxy, carboxyalkyl, cyano, formyl, halo, haloalkyl, haloalkylsulfinyl, haloalkylsulfonyl, heterocyclyl, heterocyclylamino, heterocyclylcarbonyl, heterocyclyloxy, heterocyclyloxycarbonyl, hydroxyalkyl, hydroxyl, nitro, and nitroalkyl, "Arylamino" denotes amino groups which are substituted with one or two aryl radicals, such as N-phenylamino. The "Arylaminol" radicals may be further substituted on the aryl ring portion of the radical.

"Aryloxy" embraces aryl radicals attached through an oxygen atom to other radicals.

"Aryloxyalkyl" embraces radicals having an aryl radical attached to an alkyl radical through a divalent oxygen atom.

"Benzyl" and "phenylmethyl" are interchangeable.

"Carbocycle" or "carbocyclic group" is intended to mean any stable 3 to 7 membered monocyclic or bicyclic or 7 to 14 membered bicyclic or tricyclic or an up to 26 membered polycyclic carbon ring, any of which may be saturated, partially unsaturated, or aromatic. "Substituted carbocycle" or "substituted carbocyclic group" refers to carbocyclic groups having from 1 to 5 substituents selected from a member of the group consisting of alkoxyl, substituted alkoxyl, cycloalkyl, cycloalkenyl, substituted cycloalkenyl, acyl, acylamino, acyloxyl, amino, aminoacyl, aminoacyloxyl, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Preferred examples of carbocyclic groups include, without limitation, members selected from the group consisting of adamantyl, anthracenyl, benzamidyl, benzyl, bicyclo[2.2.1]heptanyl, bicyclo[2.2.1]hexanyl, bicyclo[2.2.2]octanyl, bicyclo[3.2.0]heptanyl, bicyclo[4.3.0]nonanyl, bicyclo[4.4.0]decanyl, biphenyl, biscyclooctyl, cyclobutanyl (cyclobutyl), cyclobutenyl, cycloheptanyl (cycloheptyl), cycloheptenyl, cyclohexanedionyl, cyclohexenyl, cyclohexyl, cyclooctanyl, cyclopentadienyl, cyclopentanedionyl, cyclopentenyl, cyclopentyl, cyclopropyl, decalinyl, 1,2-diphenylethanyl, indanyl, 1-indanonyl, indenyl, naphthyl, napthlalenyl, phenyl, resorcinolyl, stilbenyl, tetrahydronaphthyl (tetralin), tetralinyl, tetralonyl, tricyclododecanyl, and the like.

"Carbonyl," whether used alone or with other terms, such as "Alkoxycarbonyl." denotes —(C=O)—.

"Carboxy" or "carboxyl," whether used alone or with other terms, such as "carboxyalkyl," denotes —CO$_2$H.

"Carboxyalkyl" embraces alkyl radicals substituted with a carboxy radical. More preferred are "lower carboxyalkyl" radicals which embrace carboxy-substituted lower alkyl radicals as defined herein. Examples of such lower carboxyalkyl radicals include carboxymethyl, carboxyethyl and carboxypropyl.

"Cellular process or activity mediated by IL-12" and "IL-12 mediated processes and activities," as used herein includes IL-12 initiated cellular processes and activities, for example, the direct stimulation of IFN-γ production by resting T cells and NK cells. This term also includes the IL-12 modulation of ongoing processes and activities, for example, the enhancement of anti-CD3 induced IFN-γ secretion. Various other IL-12-mediated processes and activities are intended to be encompassed by this term, for example, the differentiation of naïve T cells into Th1 cells; maintenance of the Th1 phenotype (e.g., high IFN-γ production, low IL-4 production); proliferation of T cell blasts; enhancement of NK cell and CTL cytolytic activity, and the like. For additional examples, see Trinchieri, *Annu. Rev. Immunol.* 13: 251–76 (1995).

"Cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include, without limitation, cyclobutenyl, cyclopentenyl and cyclohexenyl.

"Cycloalkyl" embraces saturated carbocyclic radicals having three to twelve carbon atoms. More preferred cycloalkyl radicals are "lower cycloalkyl" radicals having three to about eight carbon atoms. Examples of such radicals include, without limitation, cyclopropyl, cyclobutyl, cyclopentyl cyclohexyl, cycloheptyl, cyclooctyl, and adamantyl. "Bicycloalkyl" is intended to include saturated bicyclic ring groups such as, without limitation, [3.3.0]bicyclooctane, [4.3.0]bicyclononane, [4.4.0]bicyclodecane (decalin), [2.2.2]bicyclooctane, and so forth.

"Cycloalkylalkylene" embraces alkyl radicals substituted with a cycloalkyl radical. More preferred cycloalkylalkylene radicals are "lower cycloalkylalkylene" which embrace lower alkyl radicals substituted with a lower cycloalkyl radical as defined herein. Examples of such radicals include cyclopropylmethylene, cyclobutylmethylene, cyclopentylmethylene and cyclohexylmethylene.

"Cytokine mediated disorder" or "cytokine regulated disorder" refers to any and all disorders and disease states in which a cytokine plays a role, either by control of the disorder itself, or by causing another cytokine to be released, such as, but not limited to, IL-1, IL-6 or IL-8. A disease state in which, for instance, IL-12 is a major component, and whose production or action, is exacerbated or secreted in response to inflammatory stimuli, would therefore be considered a disorder mediated by a cytokine.

"Cytokine regulatory agent" means an agent that controls cytokine activity by enhancing, limiting, restricting, restraining, modulating or moderating the biological activity of a cytokine, including without limitation, cytokine-receptors and pathways. It should be recognized, however, that while the cytokine regulating agents generally can regulate cytokine activity, no specific mechanism of action is proposed as to how a cytokine regulatory agent acts to effect a condition characterized by altered or aberrant cytokine activity.

"Halo" or "Halogen" as used herein refers to fluoro, chloro, bromo and iodo; and "counterion" is used to represent a small, negatively charged species such as chloride, bromide, hydroxide, acetate, sulfate and the like.

"Haloalkyl" is intended to include both branched and straight-chain saturated aliphatic hydrocarbon groups having the specified number of carbon atoms, substituted with 1 or more halogen. Haloalkyl embraces radicals wherein any one or more of the alkyl carbon atoms is substituted with halo as defined herein. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Non-limiting examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

"Halosulfonyl" embraces halo radicals attached to a sulfonyl radical. Examples of such halosulfonyl radicals include chlorosulfonyl, and bromosulfonyl.

"Heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. "Heteroaryl and heterocyclyl" also embrace radicals where heterocyclyl radicals are fused with aryl radicals. Examples of such fused bicyclic radicals include benzofuran, benzothiophene, and the like. Said heterocyclyl group may have 1 to 3 substituents such as alkyl, hydroxyl, halo, alkoxy, oxo, amino and alkylamino.

"Heterocycle" or "Heterocyclic group" refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "Heterocycle" or "Heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom so long as the resulting compound is stable.

Suitable examples of such heterocyclic groups include, without limitation, acridinyl, acridonyl, adeninyl, alkylpyridinyl, alloxanyl, alloxazinyl, anthracenyl, anthranilyl, anthraquinonyl, anthrenyl, ascorbyl, azaazulenyl, azabenzanthracenyl, azabenzanthrenyl, azabenzonaphthenyl, azabenzophenanthrenyl, azachrysenyl, azacyclazinyl, azaindolyl, azanaphthacenyl, azanaphthalenyl, azaphenoxazinyl, azapinyl, azapurinyl, azapyrenyl, azatriphenylenyl, azepinyl, azetidinedionyl, azetidinonyl, azetidinyl, azinoindolyl, azinopyrrolyl, azinyl, aziridinonyl, aziridinyl, azirinyl, azocinyl, azoloazinyl, azolyl, barbituric acid, benzacridinyl, benzazapinyl, benzazinyl, benzimidazolethionyl, benzimidazolonyl, benzimidazolyl, benzisothiazolyl, benzisoxazolyl, benzocinnolinyl, benzodiazocinyl, benzodioxanyl, benzodioxolanyl, benzodioxolyl, benzofuranyl (benzofuryl), benzofuroxanyl, benzonaphthyridinyl, benzopyranonyl (benzopyranyl), benzopyridazinyl, benzopyronyl, benzoquinolinyl, benzoquinolizinyl, benzothiadiazinyl, benzothiazepinyl, benzothiazinyl, benzothiazolyl, benzothiepinyl, benzothiophenyl, benzotriazepinonyl, benzotriazolyl, benzoxadizinyl, benzoxazinyl, benzoxazolinonyl, benzoxazolyl, benzylisoquinolinyl, beta-carbolinyl, biotinyl, bipyridinyl, butenolidyl, butyrolactonyl, caprolactamyl, carbazolyl, 4a H-carbazolyl, carbolinyl, catechinyl, chromanyl, chromenopyronyl, chromonopyranyl, chromylenyl, cinnolinyl, coumarinyl, coumaronyl, decahydroquinolinyl, decahydroquinolonyl, depsidinyl, diazaanthracenyl, diazaphenanthrenyl, diazepinyl, diazinyl, diaziridinonyl, diaziridinyl, diazirinyl, diazocinyl, dibenzazepinyl, dibenzofuranyl, dibenzothiophenyl, dibenzoxazepinyl, dichromylenyl, dihydrobenzimidazolyl, dihydrobenzothiazinyl, dihydrofuranyl, dihydroisocoumarinyl, dihydroisoquinolinyl, dihydrooxazolyl, dihydropyranyl, dihydropyridazinyl, dihydropyridinyl, dihydropyridonyl, dihydropyrimidinyl, dihydropyronyl, dihydrothiazinyl, dihydrothiopyranyl, dihydroxybenzenyl, dimethoxybenzenyl, dimethylxanthinyl, dioxadiazinyl, dioxanthylenyl, dioxanyl, dioxenyl, dioxepinyl, dioxetanyl, dioxinonyl, dioxinonyl, dioxiranyl, dioxolanyl, dioxolonyl, dioxolyl, dioxopiperazinyl, diprylenyl, dipyrimidopyrazinyl, dithiadazolyl, dithiazolyl, 2H,6H-1,5,2-dithiazinyl, dithietanyl, dithiolanyl, dithiolenyl, dithiolyl, enantholactamyl, episulfonyl, flavanyl, flavanyl, flavinyl, flavonyl, fluoranyl, fluorescienyl, furandionyl, furanochromanyl, furanonyl, furanoquinolinyl, furanyl (furyl), furazanyl, furfuryl, furopyranyl, furopyrimidinyl, furopyronyl, furoxanyl, glutarimidyl, glycocyamidinyl, guaninyl, heteroazulenyl, hexahydropyrazinoisoquinolinyl, hexahydropyridazinyl, homophthalimidyl, hydantoinyl, hydrofuranyl, hydrofurnanonyl, hydroimidazolyl, hydroindolyl, hydropyranyl, hydropyrazinyl, hydropyrazolyl, hydropyridazinyl, hydropyridinyl, hydropyrimidinyl, hydropyrrolyl, hydroquinolinyl, hydrothiochromenyl, hydrothiophenyl, hydrotriazolyl, hydroxytrizinyl, imidazolethionyl, imidazolidinyl, imidazolinyl, imidazolonyl, imidazolyl, imidazoquinazolinyl, imidazothiazolyl, indazolebenzopyrazolyl, indazolyl, 1H-indazolyl, indolenyl, indolinyl, indolizidinyl, indolizinyl, indolonyl, indolyl, 3H-indolyl, indoxazenyl, inosinyl, isatinyl, isatogenyl, isoalloxazinyl, isobenzofurandionyl, isobenzofuranyl, isochromanyl, isoflavonyl, isoindolinyl (isoindolyl), isoindolobenzazepinyl, isoquinolinyl, isoquinuclidinyl, isothiazolyl, isoxazolidinyl, isoxazolinonyl, isoxazolinyl, isoxazolonyl, isoxazolyl, lactamyl, lactonyl, lumazinyl, maleimidyl, methylbenzamidyl, methylbenzoyleneureayl, methyldihydrouracilyl, methyldioxotetrahydropteridinyl, methylpurinyl, methylthyminyl, methylthyminyl, methyluracilyl, methylxanthinyl, monoazabenzonaphthenyl, morpholinyl (morpholino), naphthacenyl, naphthalenyl, naphthimidazolyl, naphthimidazopyridinedionyl, naphthindolizinedionyl, naphthodihydropyranyl, naphthofuranyl, naphthothiophenyl, naphthylpyridinyl, naphthyridinyl, octahydroisoquinolinyl, octylcarboxamidobenzenyl, oroticyl, oxadiazinyl, oxadiazolyl, oxathianyl, oxathiazinonyl, oxathietanyl, oxathiiranyl, oxathiolanyl, oxatriazolyl, oxazinonyl, oxaziranyl, oxaziridinyl, oxazolidinonyl, oxazolidinyl, oxazolidonyl, oxazolinonyl, oxazolinyl, oxazolonyl, oxazolopyrimidinyl, oxazolyl, oxepinyl, oxetananonyl, oxetanonyl, oxetanyl, oxindolyl, oxiranyl, oxolenyl, pentazinyl, pentazolyl, perhydroazolopyridinyl, perhydrocinnolinyl, perhydroindolyl, perhydropyrroloazinyl, perhydropyrrolooxazinyl, perhydropyrrolothiazinyl, perhydrothiazinonyl, perimidinyl, petrazinyl, phenanthraquinonyl, phenanthridinyl, phenanthrolinyl, phenarsazinyl, phenazinyl, phenothiazinyl, phenoxanthinyl, phenoxazinyl, phenoxazonyl, phthalazinyl, phthalideisoquinolinyl, phthalimidyl, phthalonyl, piperazindionyl, piperazinodionyl, piperazinyl, piperidinyl, piperidonyl, 4-piperidonyl, polyoxadiazolyl, polyquinoxalinyl, prolinyl, prylenyl, pteridinyl, pterinyl, purinyl, pyradinyl, pyranoazinyl, pyranoazolyl, pyranonyl, pyranopyradinyl, pyranopyrandionyl, pyranopyridinyl, pyranoquinolinyl, pyranyl, pyrazinyl, pyrazolidinyl, pyrazolidonyl, pyrazolinyl, pyrazolinonyl, pyrazolinyl, pyrazolobenzodiazepinyl, pyrazolonyl, pyrazolopyridinyl, pyrazolopyrimidinyl, pyrazolotriazinyl, pyrazolyl, pyrenyl, pyridazinyl, pyridazonyl, pyridinethionyl, pyridinonaphthalenyl, pyridinopyridinyl, pyridocolinyl, pyridoindolyl, pyridopyrazinyl, pyridopyridinyl, pyridopyrimidinyl, pyridopyrrolyl, pyridoquinolinyl, pyridyl (pyridinyl), pyrimidinethionyl, pyrimidinyl, pyrimidionyl, pyrimidoazepinyl, pyrimidopteridinyl, pyronyl, pyrrocolinyl, pyrrolidinyl, 2-pyrrolidinyl, pyrrolinyl, pyrrolizidinyl, pyrrolizinyl, pyrrolobenzodiazepinyl, pyrrolodiazinyl, pyrrolonyl, pyrrolopyrimidinyl, pyrroloquinolonyl, pyrrolyl, 2H-pyrrolyl, quinacridonyl, quinazolidinyl, quinazolinonyl, quinazolinyl, quinolinyl, quinolizidinyl, quinolizinyl, 4H-quinolizinyl, quinolonyl, quinonyl, quinoxalinyl, quinuclidinyl, quinuclidinyl, rhodaminyl, spirocoumaranyl, succinimidyl, sulfolanyl, sulfolenyl, sultamyl, sultinyl, sultonyl, sydononyl, tetrahydrofuranyl, tetrahydroisoquinolinyl, tetrahydrooxazolyl, tetrahydropyranyl, tetrahydropyrazinyl, tetrahydropyridazinyl, tetrahydropyridinyl, tetrahydroquinolinyl, tetrahydroquinoxalinyl, tetrahydrothiapyranyl, tetrahydrothiazolyl, tetrahydrothiophenyl, tetrahydrothiopyranonyl, tetrahydrothiopyranyl, tetraoxanyl, tetrazepinyl, tetrazinyl, tetrazolyl, tetronyl, thiabenzenyl, thiachromanyl, thiadecalinyl, thiadiazinyl, 6H-1,2,5-thiadiazinyl, thiadiazolinyl, thiadiazolyl, thiadioxazinyl, thianaphthenyl, thianthrenyl, thiapyranyl, thiapyronyl, thiatriazinyl, thiatriazolyl, thiazepinyl, thiazetidinyl, thiazinyl, thiaziridinyl, thiazolidinonyl, thiazolidinyl, thiazolinonyl, thiazolinyl, thiazolobenzimidazolyl, thiazolopyridinyl, thiazolyl, thienopryidinyl, thienopyrimidinyl, thienopyrrolyl, thienothiophenyl, thienyl, thiepinyl, thietanyl, thiiranyl, thiochromenyl, thiocoumarinyl, thiolanyl, thiolenyl, thiolyl, thiophenyl, thiopyranyl, thyminyl, triazaanthracenyl, triazepinonyl, triazepinyl, triazinoindolyl, triazinyl, triazolinedionyl, triazolinyl, triazolopyridinyl, triazolopyrimidinyl, triazolyl, trioxanyl, triphenodioxazinyl, triphenodithiazinyl, trithiadiazepinyl, trithianyl, trixolanyl, trizinyl, tropanyl, uracilyl, xanthenyl, xanthinyl, xanthonyl, xanthydrolyl, xylitolyl, and the like as well as N-alkoxy-nitrogen containing heterocycles. Preferred heterocyclic groups include, without limitation, members of the group consisting of acridinyl, aziridinyl, azocinyl, azepinyl, benzimidazolyl, benzodioxolanyl, benzofuranyl, benzothiophenyl, carbazole, 4a H-carbazole, chromanyl, chromenyl, cinnolinyl, decahydroquinolinyl, dioxoindolyl, furazanyl, furyl, furfuryl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthalenyl, naphthyridinyl, norbornanyl, norpinanyl, octahydroisoquinolinyl, oxazolidinyl, oxazolyl, oxiranyl, perimidinyl, phenanthridinyl, phenanthrolinyl, phenarsazinyl, phenazinyl, phenothiazinyl, phenoxathiinyl, phenoxazinyl, phenyl, phthalazinyl, piperazinyl, piperidinyl, 4-piperidonyl, piperidyl, pteridinyl, purinyl, pyranyl, pyrazinyl, pyrazinidinyl, pyrazolinyl, pyrazolyl, pyrenyl, pyridazinyl, pyridinyl, pyridyl, pyridyl, pyrimidinyl, pyrrolidinyl, 2-pyrrolidonyl, pyrrolonyl, pyrrolyl, 2H-pyrrolyl, quinazolinyl, 4H-quinolizinyl, quinolinyl, quinoxalinyl, quinuclidinyl, β-carbolinyl, tetrahydrofuranyl, tetrahydroisoquinolinyl, tetrahydroquinolinyl, tetrazolyl, 6H-1,2,5-thiadiazinyl, 2H-,6H-1,5,2-dithiazinyl, thianthrenyl, thiazolyl, thienyl, thiophenyl, triazinyl, xanthenyl, xanthinyl, and the like.

Unless otherwise constrained by the definition for the heterocyclic substituent, heterocyclic groups can be optionally substituted with 1 to 5, and preferably 1 to 3 substituents. The term "substituted heterocycle" means the above-described heterocyclic group is substituted with, for example, one or more, and preferably one or two, substituents which are the same or different which substituents can be, but not limited to, (disubstituted)amino carboxamide, (monosubstituted) amino, acyl, acylamino, acyloxyl, alkoxyamino, alkoxyl, amino, aminoacyl, aminoacyloxyl, aryl, aryloxyl, $C_1$ to $C_6$ alkyl, $C_1$ to $C_7$ acyl, $C_1$ to $C_7$ acyloxy, $C_1$ to $C_7$ alkoxy, carboxy, carboxyl, carboxylalkyl, carboxymethyl, cyano, cycloalkenyl, cycloalkyl, halogen, heteroaryl, heteroaryloxyl, heterocyclic, heterocyclooxyl, hydroxy, hydroxyamino, hydroxyl, hydroxymethyl, keto, N—(($C_1$ to $C_6$ alkyl)sulfonyl)amino, N-(phenylsulfonyl)amino groups, N—($C_1$ to $C_6$ alkyl)carboxamide, N,N-di($C_1$ to $C_6$ alkyl), nitro, oxyaminoacyl, protected (monosubstituted) amino, protected amino, protected carboxamide, protected carboxy, protected carboxymethyl, protected hydroxy, protected hydroxymethyl, protected N—($C_1$ to C6 alkyl)carboxamide, —SO, —$SO_2$-alkyl, —$SO_2$-aryl, —$SO_2$-substituted alkyl, —SO-alkyl, —SO-aryl, —SO-heteroaryl, —SO-substituted alkyl, substituted alkoxyl, substituted cycloalkenyl, substituted cycloalkyl, substituted thioalkoxyl, thioalkoxyl, thioaryloxyl, thioheteroaryloxyl, thioheterocyclooxyl, thioketo, thiol, trifluoromethyl, and $NR_aR_b$, wherein $R_a$ and $R_b$ may be the same or different and are chosen from hydrogen, optionally substituted: alkyl, cycloalkyl, alkenyl, cycloalkenyl, alkynyl, aryl, heteroaryl and heterocyclic. The term "aminosubstituted heterocyclic ring" is a heterocyclic ring substituted with at least one amino group and the term "substituted aminosubstituted heterocyclic ring is an aminosubstituted heterocyclic ring substituted with one or more of the above identified substituents for a substituted heterocyclic ring.

"Heterocyclylalkylene" embraces saturated, partially unsaturated and unsaturated heterocyclyl-substituted alkyl radicals. More preferred heterocyclylalkylene radicals are "lower heterocyclylalkylene" radicals having one to six carbon atoms and a heterocyclyl radical. Examples of such radicals include pyrrolidinylmethyl, pyridylmethyl, quinolylmethyl, thienylmethyl, furylethyl, and quinolylethyl. The heteroaryl group in said heteroaralkyl may be additionally substituted with halo, alkyl, alkoxy, haloalkyl and haloalkoxy.

"Hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical.

"Hydroxyalkyl" embraces linear or branched alkyl radicals having one to about ten carbon atoms, any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

"N-arylaminoalkyl" and "N-aryl-N-alkyl-aminoalkyl" denote amino groups that have been substituted with one aryl radical or one aryl and one alkyl radical, respectively, and having the amino group attached to an alkyl radical. Examples of such radicals include, without limitation, N-phenylaminomethyl and N-phenyl-N-methylaminomethyl.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Oxo" generally denotes a carbon atom bonded to two additional carbon atoms substituted with an oxygen atom doubly bonded to the carbon atom, thereby forming a ketone moiety.

"Pharmaceutically acceptable derivative" or "prodrug" means any pharmaceutically acceptable salt, ester, salt of an ester, or other derivative of a compound of the present invention that, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or that enhance delivery of the parent compound to a biological compartment (e.g., the brain or lymphatic system) relative to the parent species. Prodrugs are considered to be any covalently bonded carriers which release the active parent drug according to Formula I or II in vivo when such prodrug is administered to a mammalian subject. Preferred prodrugs include, without limitation, derivatives where a group that enhances aqueous solubility or active transport through the gut membrane is appended to the structure of Formula I or II. Prodrugs of the compounds of Formula I or II are prepared by modifying functional groups present in the compounds in such a way that the modifications are cleaved, either in routine manipulation or in vivo, to the parent compounds. Prodrugs include compounds of Formula I or II wherein hydroxyl, amino, sulfhydryl, or carboxyl groups are bonded to any group that, when administered to a mammalian subject, cleaves to form a free hydroxyl, amino, sulfhydryl, or carboxyl group, respectively. Examples of prodrugs include, but are not limited to, acetate, formate and benzoate derivatives of alcohol and amine functional groups in the compounds of Formula I or II, and the like.

"Pharmaceutically acceptable salts" refer to derivatives of the disclosed compounds wherein the parent compound of Formula I or II is modified by making acid or base salts of the compound of Formula I or II. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds of Formula I or II include the conventional nontoxic salts or the quaternary ammonium salts of the compounds of Formula I or II formed, for example, from nontoxic inorganic or organic acids. In particular, suitable pharmaceutically-acceptable acid addition salts of compounds of Formula I may be prepared from an inorganic acid or from an organic acid. For example, such conventional non-toxic salts include, without limitation, those derived from inorganic acids such as acetic, 2-acetoxybenzoic, 2 naphthalenesulfonilic, adipic, alginic, ascorbic, aspartic, benzoic, benzenesulfonic, bisulfic, butyric, camphoric, camphorsulfonic, carbonic, citric, cyclopentanepropionic, digluconic, dodecylsulfanilic, ethane sulfonilic, ethane disulfonic, fumaric, glucoheptanoic, glutamic, glycerophosphic, glycolic, hemisulfanoic, heptanoic, hexanoic, hydrobromic, hydrochloric, hydroiodic, 2-hydroxyethanesulfonoic, hydroxymaleic, isethionic, lactic, maleic, malic, methanesulfonic, nicotinic, nitric, oxalic, palmic, pamoic, pectinic, persulfanilic, phenylacetic, phosphoric, pivalic, propionate, propionic, salicylic, stearic, succinic, sulfamic, sulfanilic, sulfuric, tartaric, thiocyanic, toluenesulfonic, tosylic, undecanoatehydrochloric, and the like. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I or II by reacting, for example, the appropriate acid or base with a compound of the present invention. The pharmaceutically acceptable salts of the present invention can be synthesized from the compounds of Formula I or II which contain a basic or acidic moiety by conventional chemical methods, for example, by reacting the free base or acid with stoichiometric amounts of the appropriate base or acid, respectively, in water or in an organic solvent, or in a mixture of the two (nonaqueous media like ether, ethyl acetate, ethanol, isopropanol, or acetonitrile are preferred) or by reacting the free base or acid with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa., 1985, p. 1418, et al., the entire disclosure of which is incorporated herein by reference.

"Pharmaceutically effective" or "therapeutically effective" amount of a compound of the present invention is an amount that is sufficient to effect treatment, as defined herein, when administered to a mammal in need of such treatment. The amount will vary depending upon the subject and disease condition being treated, the weight and age of the subject, the severity of the disease condition, the manner of administration and the like, which can be readily determined by one of skill in the art.

"Regulate" or "Regulatory," as used herein means to control by enhancing, limiting, restricting, restraining, modulating or moderating. Such regulation includes the pleiotropic, redundant, synergistic or antagonistic effects that occur due to the activity of biological agents such as cytokines, which can affect a variety of biological functions directly or indirectly through cascade or biofeedback mechanisms.

"Stable compound", as used herein, is a compound that is sufficiently robust to survive isolation to a useful degree of purity from a reaction mixture, and formulation into an efficacious therapeutic agent, i.e., possesses stability that is sufficient to allow manufacture and that maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week. "Metabolically stable compound" denotes a compound that remains bioavailable when orally ingested by a mammal.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. It should be noted that when a substituent is listed without indicating the atom via which such substituent is bonded, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I or II, as well as the $R_2$ and $R_3$, groups substituted thereon, via any atom in such piperazinyl, piperidinyl, tetrazolyl group. Combinations of substituents and/or variables are permissible only if such combinations result in stable compounds. Further, when more than one position in a given structure may be substituted with a substituent selected from a specified group, the substituents may be either the same or different at every position. Typically, when a structure may be optionally substituted, 0–15 substitutions are preferred, 0–5 substitutions are more preferred, and 0–1 substitution is most preferred.

"Substituted alkyl," "substituted alkenyl," and "substituted alkynyl," denote that the above alkyl, alkenyl and alkynyl groups are substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_{(1-7)}$ alkoxy, $C_{(1-7)}$ acyl, $C_{(1-7)}$ acyloxy, nitro, $C_{(1-7)}$ alkyl ester, carboxy, protected carboxy, carbamoyl, carboxamide, protected carboxamide, N—($C_{(1-6)}$ alkyl)carboxamide, protected N—($C_{(1-6)}$ alkyl) carboxamide, N,N-di($C_{(1-6)}$ alkyl)carboxamide, cyano, methylsulfonylamino, thio, $C_{(1-4)}$ alkylthio or $C_{(1-4)}$ alkyl sulfonyl groups. The substituted alkyl groups may be substituted once or more, and preferably once or twice, with the same or with different substituents. Examples of "substituted alkyl" groups include 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like. Suitable examples of "substituted alkenyl" groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used. Suitable examples of "substituted" alkynyl groups include phenylacetylen-1-yl, 1-phenyl-2-propyn-1-yl and the like.

Suitable examples of "substituted phenyl" include a phenyl group substituted with one or more, and preferably one or two, moieties chosen from the groups consisting of halogen, hydroxy, protected hydroxy, cyano, nitro, $C_{(1-6)}$ alkyl, $C_{(1-7)}$ alkoxy, $C_{(1-7)}$ acyl, $C_{(1-7)}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($_{(1-6)}$ alkyl) carboxamide, protected N—($C_{(1-6)}$ alkyl)carboxamide, N,N-di($C_{(1-6)}$ alkyl) carboxamide, trifluoromethyl, N—(($C_{(1-6)}$ alkyl)sulfonyl)amino, N-(phenylsulfonyl)amino or phenyl, substituted or unsubstituted, such that, for example, a biphenyl results. Examples include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

"Sulfamyl," "Aminosulfonyl" and "sulfonamidyl" denote $NH_2O_2S$—.

"Sulfonyl," whether used alone or linked to other terms such as alkylsulfonyl, denotes respectively divalent radicals —$SO_2$—.

"Treatment" refers to any treatment of an IL-12 mediated disease or condition in a mammal, particularly a human, and includes, without limitation: (i) preventing the disease or condition from occurring in a subject which may be predisposed to the condition but has not yet been diagnosed with the condition and, accordingly, the treatment constitutes prophylactic treatment for the pathologic condition; (ii) inhibiting the disease or condition, i.e., arresting its development; (iii) relieving the disease or condition, i.e., causing regression of the disease or condition; or (iv) relieving the symptoms resulting from the disease or condition, e.g., relieving an inflammatory response without addressing the underlining disease or condition.

In view of the above non-limiting definitions, the present invention relates to a new class of pyridopyrimidine-based compounds derived from suitable starting materials. In particular, the present invention provides a pyridopyrimidine-based compound, pharmaceutically acceptable derivatives (e.g., racemic mixtures, resolved enantiomers, diastereomers, tautomers, salts and solvates thereof) or prodrugs thereof, having the following formula:

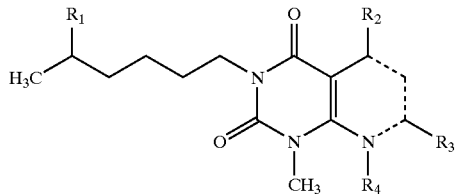

wherein:
the dashed lines, i.e., "- - - - - -", represent either a single or double bond;

$R_1$ is selected from a member of the group consisting of hydrogen, hydroxyl, methoxyl, $C_{(1-20)}$alkylaminoalkyl, N—OH, acylamino group, cyano group, sulfo, sulfonyl, sulfinyl, sulfhydryl (mercapto), sulfeno, sulfanilyl, sulfamyl, sulfamino, and phosphino, phosphinyl, phospho, phosphono and —NR$_a$R$_b$, wherein each of R$_a$ and R$_b$ may be the same or different and each is selected from the group consisting of hydrogen and optionally substituted: $C_{(1-20)}$alkyl, $C_{(1-20)}$cycloalkyl, $C_{(1-20)}$alkenyl, $C_{(1-20)}$cycloalkenyl, $C_{(1-20)}$alkynyl, aryl, heteroaryl, and heterocyclic group.

Preferably, $R_1$ is hydroxyl, methoxyl, or —NR$_a$R$_b$.

$R_2$ and $R_3$ are independently selected from a member of the group consisting of halo, thio, oxo, $C_{(1-20)}$alkyl, $C_{(1-20)}$hydroxyalkyl, $C_{(1-20)}$thioalkyl, $C_{(1-20)}$alkylthio, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraminoalkyl, $C_{(1-20)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(1-20)}$alkoxyl, $C_{(1-20)}$alkoxyalkyl, and $C_{(1-20)}$dialkoxyalkyl.

Preferably $R_2$ and $R_3$ may be independently selected from a member of the group consisting of hydrogen, halo, thio, oxo, $C_{(1-10)}$alkyl, $C_{(1-10)}$hydroxyalkyl, $C_{(1-10)}$thioalkyl, $C_{(1-10)}$alkylthio, $C_{(1-10)}$alkylamino, $C_{(1-10)}$alkylaminoalkyl, $C_{(1-10)}$aminoalkyl, $C_{(1-10)}$aminoalkoxyalkenyl, $C_{(1-10)}$aminoalkoxyalkynyl, $C_{(1-10)}$diaminoalkyl, $C_{(1-10)}$triaminoalkyl, $C_{(1-10)}$tetraminoalkyl, $C_{(1-10)}$aminotrialkoxyamino, $C_{(1-10)}$alkylamido, $C_{(1-10)}$alkylamidoalkyl, $C_{(1-10)}$amidoalkyl, $C_{(1-10)}$acetamidoalkyl, $C_{(1-10)}$alkenyl, $C_{(1-10)}$alkynyl, $C_{(1-10)}$alkoxyl, $C_{(1-10)}$alkoxyalkyl, and $C_{(1-10)}$dialkoxyalkyl.

In particular, $R_2$ and $R_3$ may be selected from the group consisting of methyl, ethyl, oxo, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, methylamino, aminomethyl, and methylphenyl.

In preferred embodiments, $R_2$ and $R_3$ may be optionally substituted with one or more members of the group consisting of hydroxyl, methyl, carboxyl, furyl, furfuryl, biotinyl, phenyl, naphthyl, amino group, amido group, carbamoyl group, cyano group, sulfo, sulfonyl, sulfinyl, sulfhydryl, sulfeno, sulfanilyl, sulfamyl, sulfamino, phosphino, phosphinyl, phospho, phosphono, N—OH, —Si(CH$_3$)$_3$, $C_{(1-3)}$alkyl, $C_{1-3}$hydroxyalkyl, $C_{1-3}$thioalkyl, $C_{1-3}$alkylamino, benzyldihydrocinnamoyl group, benzoyldihydrocinnamido group, optionally substituted heterocyclic group and optionally substituted carbocyclic group.

$R_4$ may be hydrogen or an optionally substituted member of the group consisting of $C_{(1-20)}$alkyl, $C_{(1-20)}$cycloalkyl, $C_{(1-20)}$alkenyl, $C_{(1-20)}$cycloalkenyl, $C_{(1-20)}$alkynyl, aryl, heteroaryl, and heterocyclic group.

Preferred heterocyclic groups include, without limitation, acridinyl, aziridinyl, azocinyl, azepinyl, benzimidazolyl, benzodioxolanyl, benzofuranyl, benzothiophenyl, carbazole, 4a H-carbazole, chromanyl, chromenyl, cinnolinyl, decahydroquinolinyl, dioxoindolyl, furazanyl, furyl, furfuryl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthalenyl, naphthyridinyl, norbornanyl, norpinanyl, octahydroisoquinolinyl, oxazolidinyl, oxazolyl, oxiranyl, perimidinyl, phenanthridinyl, phenanthrolinyl, phenarsazinyl, phenazinyl, phenothiazinyl, phenoxathiinyl, phenoxazinyl, phenyl, phthalazinyl, piperazinyl, piperidinyl, 4-piperidonyl, piperidyl, pteridinyl, purinyl, pyranyl, pyrazinyl, pyrazolidinyl, pyrazolinyl, pyrazolyl, pyrenyl, pyridazinyl, pyridinyl, pyridyl, pyridyl, pyrimidinyl, pyrrolidinyl, 2-pyrrolidonyl, pyrrolonyl, pyrrolyl, 2H-pyrrolyl, quinazolinyl, 4H-quinolizinyl, quinolinyl, quinoxalinyl, quinuclidinyl, β-carbolinyl, tetrahydrofuranyl, tetrahydroisoquinolinyl, tetrahydroquinolinyl, tetrazolyl, 6H-1,2,5-thiadiazinyl, 2H-,6H-1,5,2-dithiazinyl, thianthrenyl, thiazolyl, thienyl, thiophenyl, triazinyl, xanthenyl and xanthinyl.

Preferred carbocyclic groups include, without limitation, adamantyl, anthracenyl, benzamidyl, benzyl, bicyclo[2.2.1] heptanyl, bicyclo[2.2.1]hexanyl, bicyclo[2.2.2]octanyl, bicyclo[3.2.0]heptanyl, bicyclo[4.3.0]nonanyl, bicyclo [4.4.0]decanyl, biphenyl, biscyclooctyl, cyclobutyl, cyclobutenyl, cycloheptyl, cycloheptenyl, cyclohexanedionyl, cyclohexenyl, cyclohexyl, cyclooctanyl, cyclopentadienyl, cyclopentanedionyl, cyclopentenyl, cyclopentyl, cyclopropyl, decalinyl, 1,2-diphenylethanyl, indanyl, 1-indanonyl, indenyl, naphthyl, napthlalenyl, phenyl, resorcinolyl, stilbenyl, tetrahydronaphthyl, tetralinyl, tetralonyl, and tricyclododecanyl.

If substituted, the heterocyclic group or carbocyclic group is substituted with one or more members of the group consisting of halo, hydroxyl, nitro, SO$_2$NH$_2$, $C_{(1-6)}$alkyl, $C_{(1-6)}$haloalkyl, $C_{(1-6)}$alkoxyl, $C_{(1-11)}$alkoxyalkyl, $C_{(1-6)}$alkylamino, and $C_{(1-6)}$aminoalkyl.

In accordance with the principles of the present invention, the novel therapeutic compounds disclosed herein may contain one or more asymmetrically substituted carbon atoms and, thus, may occur as racemates and racemic mixtures, single enantiomers, diastereomeric mixtures and individual diastereomers. Each stereogenic carbon may be of the R or S configuration. Many geometric isomers of olefins, C—N double bonds, and the like can also be present in the compounds described herein, and all such stable isomers are contemplated in the present invention. It is well known in the art how to prepare optically active forms, such as by resolution of racemic forms or by synthesis from optically active starting materials. All chiral, diastereomeric, racemic forms and all geometric forms of a structure are intended to be encompassed within the present invention unless a specific stereochemistry or isomer form is specifically indicated. The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphor-sulfonic acid, tartaric acid, lactic acid and the like or chiral bases such as rucine, cinchona alkaloids and their derivatives and the like.

Various polymorphs of the compound of general Formulae I or II form part of the present invention and may be prepared by crystallization of the compound under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffractogram or such other techniques.

The compounds of the present invention may be modified by appending appropriate functionalites to enhance selective biological properties. Such modifications are known in the art and include, without limitation, those which increase penetration into a given biological compartment (e.g., blood, lymphatic system, central nervous system), increase oral or intravenous bioavailability, increase solubility to allow administration by injection, alter metabolism, alter rate of excretion, etc. The present invention also comprises the tautomeric forms of compounds of the present invention.

The present invention also envisions the quaternization of any basic nitrogen-containing groups of the compounds disclosed herein. The basic nitrogen can be quaternized with any agents known to those of ordinary skill in the art including, without limitation, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In addition to their structural characteristics, the novel pyridopyrimidine-based compounds of the invention can regulate the aberrant or altered expression of one or more cytokines that occurs in various conditions, including, for example, pathologies, immune responses and inflammatory responses, which are characterized, in part, by aberrant or altered cytokine activity and, therefore, are amenable to regulation by one or more cytokine regulatory agents. A skilled artisan or scientist using routine protocols or assays, such as the assays disclosed in the Examples below or in the literature, may readily confirm the utility of the compounds disclosed herein.

Without being bound by the above general structural descriptions/definitions, preferred compounds of the present invention having usefulness as cytokine regulating agents according to the present invention, include, but are not limited to the following compounds. It will be appreciated, as noted above, that where an R or S enantiomer is exemplified for each particular compound, the corresponding S or R enantiomer, respectively, is also intended even though it may not be specifically shown below.

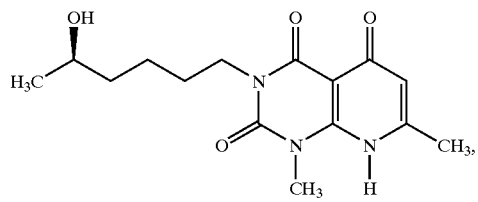

-continued

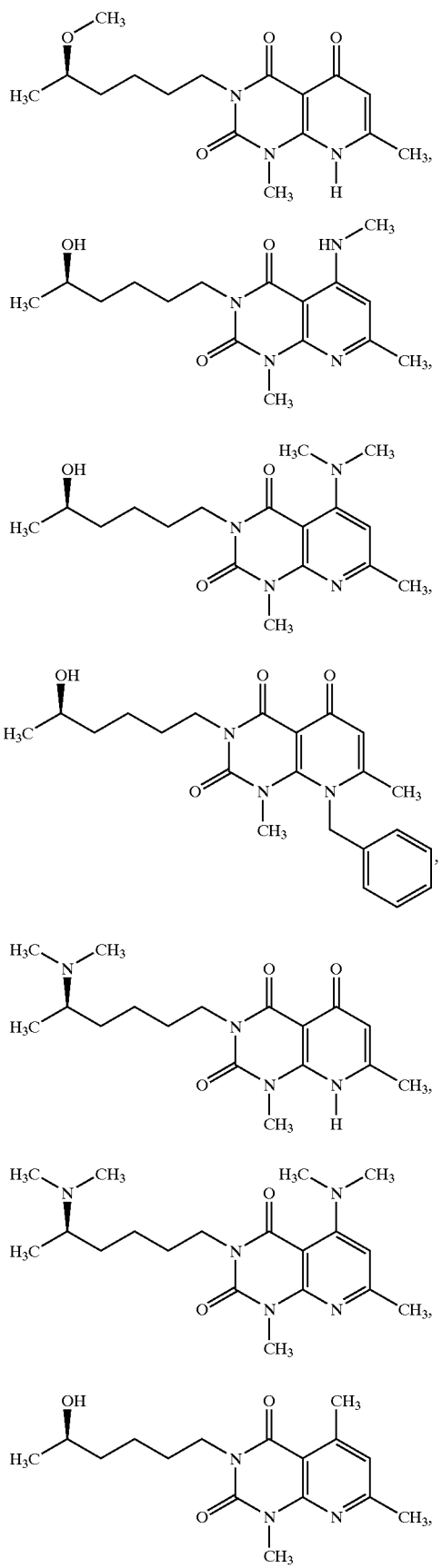

-continued

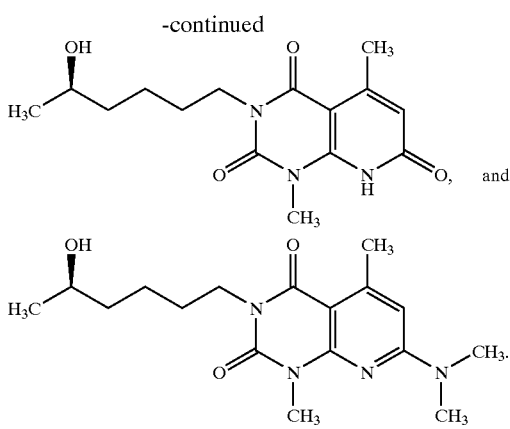

METHODS OF USE

The present invention is also directed to a method for inhibiting cytokine signaling in a mammal having, for example, an inflammatory or anti-inflammatory response. The methods of the present invention generally comprise administering a pharmaceutically or therapeutically effective amount of a compound as described herein to a patient suffering from a disease or condition mediated by one or more cytokines. The patient may be a human mammal. For example, a patient will need treatment when exhibiting a deleterious response in the course of a disease condition mediated by Th1, T1, Th2 or T2 cells. Such need is determinable by skilled clinicians and investigators in the medical arts. Besides being useful for human treatment, these compounds are also useful for veterinary treatment of companion animals, exotic animals and farm animals, including mammals, rodents, and the like. More preferred animals include horses, dogs, and cats.

Preferred disease conditions characterized by altered or aberrant cytokine activity, and hence, considered treatable by the present inventive compounds include, but are not limited to: (1) inflammatory diseases or disorders, such as, for example, arthritis, asthma, chronic inflammatory diseases, chronic intestinal inflammation, psoriasis, septic shock, septicemia, allergic contact dermatitis, ankylosing spondylitis and adult respiratory distress syndrome; (2) autoimmune diseases or disorders or other patho-immunogenic diseases or reactions, such as, for example, allergic reactions or anaphylaxis; allergic encephalomyelitis, amyotrophic lateral sclerosis, bullous pemphigold, Celiac disease, chronic active hepatitis, chronic thyroiditis, gastritis, Goodpastures syndrome, graft-versus-host disease (acute and/or chronic), glomerulonephritis; hemolytic anemia, immune thrombocytopenia purpura, inflammatory bowel disease (e.g., Crohn's Disease and ulcerative colitis), isopathic thrombocytopenic purpura, juvenile arthritis, lupus disorders (e.g., systemic lupus erythematosus), male infertility (autoimmune), multiple sclerosis, myasthenia gravis, neutropenia, pemphigus vulgaris, parasitic mediated immune dysfunctions (e.g. Chagas' Disease), pemphigus vulgaris, pernicious anemia, polyarteritis nodosa, primary antiphospholipid syndrome, primary biliary cirrhosis, primary Sjogren's syndrome, Reiter's disease, rheumatic fever, rheumatoid arthritis, sarcoidosis, scleroderma, thrombocytopenia, Sjorgens disease, sympathetic ophthalmia, thyroid diseases (e.g., Graves' and Hashimoto's disease), Type-1 (IDDM) and Type-2 (NIDDM) diabetes mellitus, uveitis, and viral myocarditis (Cocksakie B virus response); (3) neurodegenerative diseases such as, for example, Alzheimer's disease, Parkinson's disease, and primary lateral sclerosis; (4) chronic lymphocytic leukemia (CLL), hairy cell leukemia, prolymphocytic leukemia, well differentiated lymphocytic lymphomas, infectious mononucleosis, human immunodeficiency virus; (5) adverse reactions associated with cancer chemotherapy; (6) diseases such as atherosclerosis and diabetes that are believed to be mediated by free radicals and nitric oxide action; (7) bacterial endotoxic sepsis and related shock; (8) pain; (9) type 1 hypersensitivity allergic reactions such as asthma, hay fever, eczema, urticaria, food allergy and atopic dermatitis; (10) cachexia; and (11) angiogenesis, including neoplasia; metastasis; etc. The methods of using the compounds of the present invention are particularly useful in the treatment of autoimmune diseases, MS, diabetes mellitus (Type-1 or -2) or asthma.

In a still further aspect, the present invention is directed to a method for treating a Th1 or Th2 cell-mediated response in a mammal in need of such treatment, the method comprising: administering to the mammal a therapeutically effective amount of the compound of the present invention, wherein said compound is capable of inhibiting an IL-12 or IL-4 mediated cellular process or activity, thereby inhibiting the response.

In another preferred embodiment, the present invention includes a method for preventing or treating type-1 or type-2 diabetes. Diabetes is one of the most prevalent chronic disorders worldwide with significant personal and financial costs for patients and their families, as well as for society. Diabetes mellitus is characterized by a broad array of physiologic and anatomic abnormalities, for example, altered glucose disposition, hypertension, retinopathy, abnormal platelet activity, aberrations involving large, medium and small sized vessels, and other problems encountered in diabetic patients. Diabetics are generally divided into two categories. Patients who depend on insulin for the prevention of ketoacidosis have insulin-dependent diabetes mellitus (IDDM) or Type-1 diabetes. Diabetics who do not depend on insulin to avoid ketoacidosis have non-insulin-dependent diabetes mellitus (NIDDM) or Type-2 diabetes. NIDDM is the form of diabetes mellitus that occurs predominantly in adults in whom adequate production of insulin is available for use, yet a defect exists in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver. It has been shown that for some people with diabetes a genetic predisposition results in a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

Reports indicate that insulin secretion is often enhanced early-on, presumably as compensation for the insulin resistance. People who actually develop NIDDM appear to do so because their pancreatic β-cells eventually fail to maintain sufficient insulin secretion to compensate for the insulin resistance. Mechanisms responsible for the β-cell failure have not been identified, but may be related to the chronic demands placed on the β-celis by peripheral insulin resistance and/or to the effects of hyperglycemia to impair β-cell function. The β-cell failure could also occur as an independent, inherent defect in "pre-diabetic" individuals.

Furthermore, it has been suggested that a link exists between obesity and non-insulin dependent diabetes mellitus (NIDDM) (Hotamisligil and Spiegelman, *Diabetes* 43:1271–1278 (1994a)). As such, the present invention is useful for decreasing the weight of an obese subject to prevent or alleviate the symptoms associated with NIDDM. Increased TNF expression has been detected in the adipose tissue of obese individuals and has been suggested to have a role in the appearance of NIDDM in these individuals (Hotamisligil et al., *J. Clin. Invest*, 95:2409–2415 (1995)). However, efforts to neutralize TNF activity using an antibody that binds the TNF receptor did not result in significant weight loss when examined in a rat obesity/diabetes model (Hotamisligil et al., *J. Clin Invest*, 94:1543–1549 (1994b)). Because of at least their cytokine regulating activity, the compounds of the present invention are particularly useful for treating diabetes and associated obesity. Furthermore, insulin secretory defects in NIDDM may be associated with defects in fatty acid metabolism. The compounds of the present invention are modulators of fatty acid metabolism and therefore play a role in ameliorating the effects of NIDDM by affecting insulin secretion and glucose tolerance. Thus, the present invention relates to novel antidiabetic compounds of the present invention, their tautomeric forms, their derivatives, their stereoisomers, their polymorphs, their pharmaceutically acceptable salts, their pharmaceutically acceptable solvates and pharmaceutically acceptable compositions containing them, as well as a method for preventing or treating diabetes mellitus, types-1 or -2, comprising the step of administering to a subject in need thereof a therapeutically effective amount of the compound of the present invention.

The present invention further encompasses a method of screening for substances or targets (e.g., proteins, peptides, small molecules) that enhance or inhibit the cell activity of cytokines. In a preferred embodiment, the present invention comprises a method for inhibiting a cellular process or activity mediated or regulated by a cytokine, such as IL-12 (Th1 or T1 cell differentiation) or IL-4 (Th2 or T2 cell differentiation), the method comprising:

(a) contacting cytokine responsive cells with a compound of the present invention, as described above; and (b) determining that the cellular process or activity mediated or regulated by the cytokine is inhibited.

The compounds of the present invention are also useful for inhibiting cytokine mediated signaling in other applications such as in vitro systems and in vivo animal models of cytokine mediated diseases. As such, the present invention further encompasses a method of screening for substances (e.g., proteins, peptides, small molecules) that enhance or inhibit the cell activity of cytokines. Accordingly, the present invention encompasses a pre-packaged kit comprising a compound of the present invention, as described herein, for use in such applications.

PHARMACEUTICAL COMPOSITIONS AND DOSAGE

Also embraced within this invention is a class of pharmaceutical compositions comprising the active compounds of this invention in association with one or more non-toxic, pharmaceutically-acceptable carriers and/or diluents and/or adjuvants (collectively referred to herein as "carrier" materials) and, if desired, other active ingredients. Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration or by any means that produces contact of the active agent with the agent's site of action in the body of a mammal. They can be administered by any conventional means available for use in conjunction with pharmaceuticals, either as individual therapeutic agents or in a combination of therapeutic agents readily determinable by the skilled artisan. They can be administered alone, but are generally administered with a pharmaceutical carrier selected on the basis of the chosen route of administration and standard pharmaceutical practice. Suitable pharmaceutical carriers are described in Remington's Pharmaceutical Sciences.

In particular, the compounds of the present invention can be administered in such oral dosage forms as tablets, capsules (each of which includes sustained release or timed release formulations), pills, powders, granules, elixirs, tinctures, suspensions, syrups, and emulsions. Preparations for oral administration may be suitably formulated to give controlled release of the active compound. Likewise, they may also be administered in intravenous (bolus or infusion), intraperitoneal, subcutaneous, or intramuscular form, all using dosage forms well known to those of ordinary skill in the pharmaceutical arts. The compounds of the present invention can be administered in intranasal form via topical use of suitable intranasal vehicles, or via transdermal routes, using those forms of transdermal skin patches well known to those of skill in that art. To be administered in the form of a transdermal delivery system, the dosage administration will, of course, be continuous rather than intermittent throughout the dosage regimen. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. For parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A n ordinarily skilled physician or veterinarian can readily determine and prescribe the effective amount of the drug required to prevent, counter, or arrest the progress of the condition. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. By way of general guidance, the daily oral dosage of each active ingredient, when used for the indicated effects, will range between about 0.001 to 1000 mg/kg of body weight, preferably between about 0.01 to about 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

In the methods of the present invention, the inventive compounds can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices. For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include, without limitation, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. The preparations may also contain buffer salts, flavoring, coloring and sweetening agents, as deemed appropriate by a skilled artisan.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include, without limitation, polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Useful pharmaceutical dosage-forms for administration of the compounds of this invention can be illustrated, without limitation, as follows:

Capsules. A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules. A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets. A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable. A parenteral composition suitable for administration by injection is prepared by stirring 1.5% by weight of active ingredient in 10% by volume propylene glycol and water. The solution is made isotonic with sodium chloride and sterilized.

Suspension. An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent such as, for example, a corticosteroid, analgesics, etc. The compounds of the present invention and such second therapeutic agent can be administered separately or as a physical combination in a single dosage unit, in any dosage form and by various routes of administration, as described above. The compounds of the present invention may be formulated together with the second therapeutic agent in a single dosage unit (that is, combined together in one capsule, tablet, powder, or liquid, etc.). When the compounds of the present invention and the second therapeutic agent are not formulated together in a single dosage unit, they may be administered essentially at the same time, or in any order; for example, the compounds of the present invention may be administered first, followed by administration of the second agent. When not administered at the same time, preferably the administration of a compound of the present invention and the second therapeutic agent occurs less than about one hour apart, more preferably less than about 5 to 30 minutes apart. Preferably the route of administration is oral. Although it is preferable that the inventive compound and the second therapeutic agent are both administered by the same route (that is, for example, both orally), if desired, they may each be administered by different routes and in different dosage forms (that is, for example, one component of the combination product may be administered orally, and another component may be administered intravenously). The present compounds may be partially or completely in place of other conventional anti-inflammatory agents, such as together with steroids, cyclooxygenase-2 inhibitors, NSAIDs, DMARDS, immunosuppressive agents, 5-lipoxygenase inhibitors, LTB4 antagonists, LTA4 hydrolase inhibitors and the like.

The dosage when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of a compound of the present invention when administered in combination with the second therapeutic agent will be readily ascertainable by a medical practitioner skilled in the art, once armed with the present disclosure.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

SYNTHESIS

Compounds of the present invention can be synthesized using the methods described in the Examples below, which are preferred, as well as by synthetic methods known in the art of synthetic organic chemistry, or variations thereon as readily appreciated and readily performable by those skilled in the art. The various synthetic steps described herein may be performed in an alternate sequence or order to give the desired compounds. Moreover, the synthesis Examples described herein are not intended to comprise a comprehensive list of all means by which the compounds described and claimed in this patent application may be synthesized.

As can be appreciated by the skilled artisan, the preferred synthetic schemes described in the Examples below are not intended to comprise a comprehensive list of all means by which the compounds described and claimed herein may be synthesized. It should be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described may be performed in an alternate sequence or order to give the desired compounds.

EXAMPLES

The present invention will be further illustrated in the following, non-limiting Examples. The Examples are illustrative only and do not limit the claimed invention regarding the materials, conditions, process parameters and the like recited herein.

Example 1

Synthesis of

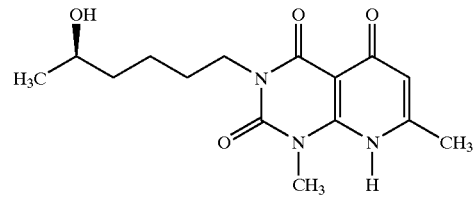

(R)-1,7-Dimethyl-3-(5-hydroxyhexyl)pyrido[2,3-d]pyrimidine-2,4,5(1H,3H,8H)-trione (CT-12480)

A 1 liter round bottomed flask was charged with 95% sodium hydride (5.5 g, 220 mmol), dry dimethylsulfoxide (400 ml), and was cooled in an ice bath. 6-Amino-1-methyluracil (28.2 g, 200 mmol) was added slowly in portions. After evolution of hydrogen gas had subsided, the mixture was warmed to room temperature and stirred until the solid had completely dissolved (1 hour). (R)-5-Acetoxy-1-chlorohexane (37.5 g, 210 mmol), prepared as described by Klein, J. P.; Leigh, A. J.; Michnick, J.; Kumar, A. M.; Underiner, G. E. Asymmetric Synthesis of Chiral Secondary Alcohols, U.S. Pat. No. 5,629,423 (May 13, 1997), was added slowly. The mixture was heated at 80° C. for 18 hours, and after cooling to room temperature, was treated with saturated aqueous sodium chloride solution (1 L) and extracted with ethyl acetate (4×200 ml). The combined extracts were washed again with saturated aqueous sodium chloride solution, dried over sodium sulfate, and concentrated under reduced pressure. The residue was treated with diethyl ether (100 ml) and stirred for 18 hours. The solid was filtered, rinsed with diethyl ether, and dried under vacuum to provide (R)-3-(5-acetoxyhexyl)-6-amino-1-methyluracil (37 g, 65% yield) as a beige powder. $^1$H NMR (300 MHz, CDCl$_3$) δ 1.17 (d, 3H), 1.25–1.71 (m, 6H), 2.00 (s, 3H), (t, 2H), 4.75–4.90 (m, 3H), 4.95 (s, 1H).

A mixture of (R)-3-(5-acetoxyhexyl)-6-amino-1-methyluracil (500 mg, 1.77 mmol), 1,2-dichloroethane (5 ml) and diketene (0.14 ml, 1.77 mmol) was heated at reflux for 18 hours. Another portion of diketene (0.2 ml) was added and the mixture was heated at reflux for an additional 18 hours. After cooling to room temperature, the mixture was concentrated under reduced pressure. The residue was purified by column chromatography on silica gel eluting with ethyl acetate-hexane (1:1) to provide (R)-3-(5-acetoxyhexyl)-1,7-dimethylpyrido[2,3-d]pyrimidine-2,4,5(1H,3H,8H)-trione (300 mg, 49% yield) as an oil. $^1$H NMR (300 MHz, CDCl$_3$) δ 1.20 (d, 3H), 1.25–1.71 (m, 6H), 2.00 (s, 3H), 2.46 (s, 3H), 3.62 (s, 3H), 4.00 (t, 2H), 4.86 (sextet, 1H), 6.49 (s, 1H), 12.15 (s, 1H). $^{13}$C NMR (75 MHz, CDCl$_3$) δ 19.64, 20.96, 22.46, 25.02, 27.19, 29.15, 35.19, 40.67, 70.29, 94.48, 105.71, 150.09, 150.73, 164.92, 165.18, 167.82, 170.15.

Alternatively, (R)-3-(5-acetoxyhexyl)-1,7-dimethylpyrido[2,3-d]pyrimidine-2,4,5(1H,3H,8H)-trione was prepared as follows: To a mixture of (R)-3-(5-acetoxyhexyl)-6-amino-1-methyluracil (2.1 g, 7.41 mmol) in xylenes (70 ml) heated to 160° C. was added over 30 minutes a solution of 2,2,6-trimethyl-4H-1,3-dioxin-4-one (2.0 ml, 15.3 mmol) in xylenes (30 ml). After stirring at 160° C. for 20 minutes, the mixture was cooled to room temperature and concentrated under reduced pressure. The residue was purified by column chromatography on silica gel eluting with 20% ethyl acetate-toluene to afford (R)-3-(5-acetoxyhexyl)-1,7-dimethylpyrido[2,3-d]pyrimidine-2,4,5(1H,3H,8H)-trione (1.37 g, 53% yield) as a clear oil. $^1$H NMR (300 MHz, CDCl$_3$) δ 1.20 (d, 3H), 1.25–1.71 (m, 6H), 2.00 (s, 3H), 2.46 (s, 3H), 3.62 (s, 3H), 4.00 (t, 2H), 4.86 (sextet, 1H), 6.49 (s, 1H), 12.15 (s, 1H). $^{13}$C NMR (75 MHz, CDCl$_3$) δ 19.64, 20.96, 22.46, 25.02, 27.19, 29.15, 35.19, 40.67, 70.29, 94.48, 105.71, 150.09, 150.73, 164.92, 165.18, 167.82, 170.15.

A mixture of (R)-3-(5-acetoxyhexyl)-1,7-dimethylpyrido[2,3-d]pyrimidine-2,4,5(1H,3H,8H)-trione (100 mg, 0.286 mmol), diethyl ether (0.5 ml) and 3 M aqueous hydrochloric acid solution (5 ml) was stirred at room temperature for 18 hours. After treating with saturated aqueous sodium bicarbonate (20 ml), the mixture was extracted with diethyl ether (2×20 ml). The combined extracts were dried over sodium sulfate, and concentrated under vacuum to afford (R)-1,7-dimethyl-3-(5-hydroxyhexyl)pyrido[2,3-d]pyrimidine-2,4,5(1H,3H,8H)-trione (81 mg, 92% yield) a white powder. $^1$H NMR (300 MHz, CDCl$_3$) δ 1.17 (d, 3H), 1.30–1.52 (m, 3H), 1.54–1.70 (m, 4H), 2.45 (s, 3H), 3.62 (s, 3H), 3.77 (m, 1H), 4.00 (t, 2H), 6.49 (s, 1H), 12.15 (s, 1H).

Example 2

Synthesis of

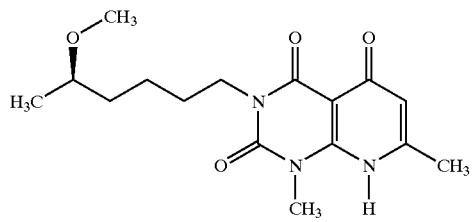

(R)-1,7-Dimethyl-3-(5-methoxyhexyl)pyrido[2,3-d]pyrimidine-2,4,5(1H,3H,8H)-trione (CT-13415)

A mixture of (R)-5-acetoxy-1-chlorohexane (10.0 g, 56 mmol), methanol (50 ml) and diethyl ether (50 ml) was sparged with hydrogen chloride gas for 5 minutes and stirred at room temperature for 18 hours. After concentration under reduced pressure, remaining volatiles were removed via coevaporation with heptanes (3×50 ml) to provide (R)-1-chloro-5-hydroxyhexane which was used immediately in the next step.

A mixture of (R)-1-chloro-5-hydroxyhexane, dimethylformamide (100 ml), powdered potassium carbonate (1 g), iodomethane (15.9 g, 112 mmol) and sodium hydride (2.0 g, 84 mmol) were combined was heated at 40° C. for 30 minutes. After cooling to room temperature, water (100 ml) was added cautiously and the mixture was extracted with hexanes (2×100 ml). The combined extracts were concentrated under vacuum and the residue was purified by column chromatography on silica gel eluting with hexanes followed by 10% ethyl acetate-hexanes to afford (R)-1-chloro-5-methoxyhexane (3.1 g, 43% yield for 2 steps) as a clear oil. $^1$H NMR (300 MHz, CDCl$_3$) δ 1.15 (d, 3H), 1.36–1.56 (m, 4H), 1.70–1.84 (m, 2H), 3.28 (s, 3H), 3.29 (m, 1H), 3.52 (t, 2H).

A mixture of 6-amino-1-methyluracil (141 mg, 1.0 mmol), (R)-1-chloro-5-methoxyhexane (150 mg, 1.0 mmol), dimethylsulfoxide (2 ml) and sodium hydride (30 mg, 1.2 mmol) was heated to 90° C. for 18 hours. After cooling to room temperature, the mixture was treated with water (7 ml) and extracted with ethyl acetate. The extract was dried over sodium sulfate and concentrated under reduced pressure. The residue was purified by column chromatography on silica gel eluting with ethyl acetate followed by 5% methanol-ethyl acetate to provide (R)-6-amino-3-(5-methoxyhexyl)uracil (152 mg, 60% yield) as an oil.

A mixture of (R)-6-amino-3-(5-methoxyhexyl)uracil (152 mg, 0.595 mmol), diketene (0.07 ml, 0.89 mmol), hydroquinone (7 mg, 0.06 mmol) and benzene (5 ml) was heated at reflux for 3 hours. Another portion of diketene (0.2 ml) was added and heating at reflux was continued for 18 hours. After cooling to room temperature, the mixture was concentrated under reduced pressure. The residue was partitioned between water (20 ml) and ethyl acetate (20 ml). The organic layer was concentrated under reduced pressure and the residue was purified by column chromatography on silica gel eluting with 20% ethyl acetate-toluene to provide (R)-1,7-dimethyl-3-(5-methoxyhexyl)pyrido[2,3-d]pyrimidine-2,4,5(1H,3H,8H)-trione (101 mg, 53% yield) as an oil which crystallized on standing. $^1$H NMR (300 MHz, CDCl$_3$) δ 1.13 (d, 3H), 1.30–1.79 (m, 6H), 2.48 (s, 3H), 3.29 (m, 1H), 3.30 (s, 3H), 3.75 (s, 3H), 4.02 (t, 2H), 6.50 (s, 1H), 12.21 (s, 1H).

Example 3

Synthesis of

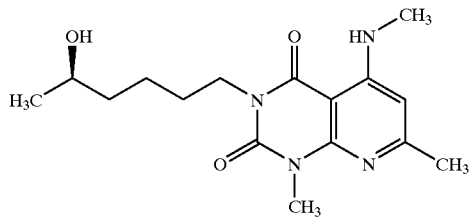

(R)-1,7-Dimethyl-3-(5-hydroxyhexyl)-5-(N-methylamino)pyrido[2,3-d]pyrimidine-2,4(1H,3H)-dione (CT-30102)

To a mixture of (R)-3-(5-acetoxyhexyl)-1,7-dimethylpyrido[2,3-d]pyrimidine-2,4,5(1H,3H,8H)-trione (415 mg, 1.19 mmol), dichloromethane (20 ml) and pyridine (1 ml), cooled in an ice bath, was added trifluoromethanesulfonic anhydride (0.6 ml, 3.6 mmol). After 1 hour, the cooling bath was removed and the mixture was concentrated under reduced pressure. The residue was purified by short column chromatography on silica gel eluting with ethyl acetate-hexanes (1:1) to provide (R)-3-(5-acetoxyhexyl)-1, 7-dimethyl-5-trifluoromethanesulfonyloxypyrido[2,3-d] pyrimidine-2,4(1H,3H)-dioneas a brown oil. $^1$H NMR (300 MHz, CDCl$_3$) δ 1.20 (d, 3H), 1.30–1.73 (m, 6H), 2.03 (s, 3H), 2.65 (s, 3H), 3.70 (s, 3H), 4.06 (t, 2H), 4.88 (sextet, 1H), 6.83 (s, 1H).

A mixture of (R)-3-(5-acetoxyhexyl)-1,7-dimethyl-5-trifluoromethanesulfonyloxypyrido[2,3-d]pyrimidine-2,4 (1H,3H)-dione (30 mg, 0.062 mmol), methanol (1 ml), and 40% aqueous methylamine (1 ml) was stirred at room temperature for 10 minutes. Concentration under reduced pressure provided crude (R)-3-(5-acetoxyhexyl)-1,7-dimethyl-5-(N-methylamino)pyrido[2,3-d]pyrimidine-2,4 (1H,3H)-dione which was used immediately in the next step.

To the crude (R)-3-(5-acetoxyhexyl)-1,7-dimethyl-5-(N-methylamino)pyrido[2,3-d]pyrimidine-2,4(1H,3H)-dione was added a solution of potassium hydroxide (100 mg) in 20% water-methanol (2 ml). After stirring at room temperature for 1 hour, the mixture was concentrated under reduced pressure to remove methanol. The aqueous mixture was extracted with ethyl acetate (10 ml). The extract was dried over sodium sulfate and the residue was purified by short column chromatography eluting with ethyl acetate to provide (R)-1,7-dimethyl-3-(5-hydroxyhexyl)-5-(N-methylamino)pyrido[2,3-d]pyrimidine-2,4(1H,3H)-dione 15 mg, 76% yield for 2 steps) as an oil. $^1$H NMR (300 MHz, benzene d$_6$) δ 0.98 (d, 3H), 1.25–1.50 (m, 4H), 1.70–1.82 (m, 2H), 2.18 (d, 3H), 2.27 (s, 3H), 3.49–3.58 (m, 1H), 3.60 (s, 3H), 4.11 (t, 2H), 5.70 (s, 1H), 9.09 (broad s, 1H).

Example 4

Synthesis of

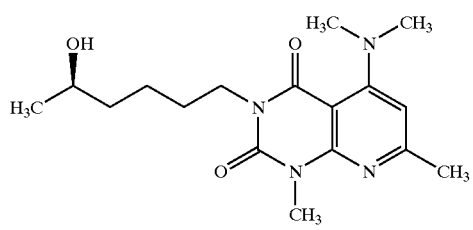

(R)-1,7-Dimethyl-5-(N,N-dimethylamino)-3-(5-hydroxyhexyl)pyrido[2,3-d]pyrimidine-2,4(1H,3H)-dione (CT-30103)

A pressure tube was charged with (R)-3-(5-acetoxyhexyl)-1,7-dimethyl-5-trifluoromethanesulfonyloxypyrido[2,3-d]pyrimidine-2,4 (1H,3H)-dione (100 mg, 0.208 mmol) and tetrahydrofuran (1 ml). After cooling to 0° C., dimethylamine gas was introduced until approximately 1 ml had collected. The tube was sealed and heated at 55° C. for 18 hours. After cooling to room temperature, the tube was carefully vented and the dimethylamine was evaporated to provide crude (R)-3-(5-acetoxyhexyl)-1,7-dimethyl-5-(N,N-dimethylamino)pyrido [2,3-d]pyrimidine-2,4(1H,3H)-dione.

To crude (R)-3-(5-acetoxyhexyl)-1,7-dimethyl-5-(N,N-dimethylamino)pyrido[2,3-d]pyrimidine-2,4(1H,3H)-dione was added a solution of potassium hydroxide (100 mg) in 10% water-methanol (2.2 ml). After stirring at room temperature for 2 hours, the mixture was concentrated under reduced pressure. The residue was treated with saturated aqueous sodium chloride solution (10 ml) and ethyl acetate (10 ml). The organic layer was dried over sodium sulfate and concentrated under reduced pressure to afford (R)-1,7-dimethyl-5-(N,N-dimethylamino)-3-(5-hydroxyhexyl) pyrido[2,3-d]pyrimidine-2,4(1H,3H)-dione (55 mg, 79% yield for 2 steps) as an oil. $^1$H NMR (300 MHz, benzene d$_6$) δ 1.13 (d, 3H), 1.20–1.50 (m, 4H), 1.56–1.72 (m, 2H), 2.11 (s, 3H), 3.40 (s, 3H), 3.55 (m, 1H), 3.90 (t, 2H), 6.21 (s, 1H), 7.15 (s, 1H).

Example 5

Synthesis of

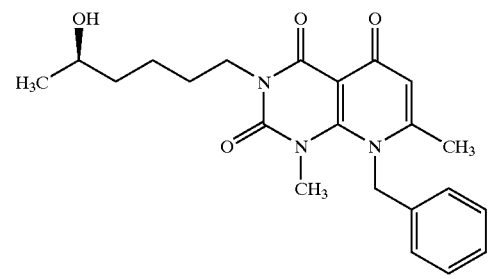

(R)-8-Benzyl-1,7-dimethyl-3-(5-hydroxyhexyl) pyrido[2,3-d]pyrimidine-2,4,5(1H,3H,8H)-trione (CT-30059)

A mixture of (R)-3-(5-acetoxyhexyl)-1,7-dimethylpyrido [2,3-d]pyrimidine-2,4,5(1H,3H,8H)-trione (1.84 g, 5.27 mmol), acetonitrile (20 ml), benzyl bromide (0.95 ml, 7.91 mmol) and potassium carbonate (2.19 g, 15.8 mmol) was stirred at 50° C. for 2 hours. After cooling to room temperature, the mixture was concentrated under reduced pressure. The residue was treated with water (50 ml) and extracted with ethyl acetate (50 ml). The organic extract was concentrated under reduced pressure to afford crude (R)-3-(5-acetoxyhexyl)-8-benzyl-1,7-dimethylpyrido[2,3-d] pyrimidine-2,4,5(1H,3H,8H)-trione.

37% Aqueous hydrochloric acid (5 ml) was added to a solution of the crude (R)-3-(5-acetoxyhexyl)-8-benzyl-1,7-dimethylpyrido[2,3-d]pyrimidine-2,4,5(1H,3H,8H)-trione in methanol (20 ml). After stirring at room temperature for 18 hours, the solution was concentrated under reduced pressure. The residue was treated with water (20 ml) and extracted with ethyl acetate (2×20 ml). The combined extracts were concentrated under reduced pressure to provide an oil which solidified on standing. The solid was recrystallized (ethyl acetate-hexanes) to afford (R)-8-Benzyl-1,7-dimethyl-3-(5-hydroxyhexyl)pyrido[2,3-d] pyrimidine-2,4,5(1H,3H,8H)-trione (1.26 g, 60% yield for 2 steps) as a white powder. $^1$H NMR (300 MHz, CDCl$_3$) δ 1.19 (d, 3H), 1.35–1.52 (m, 4H), 1.54–1.70 (m, 2H), 2.47 (s,3H), 3.63 (s, 3H), 3.78 (m, 1H), 4.05 (t, 2H), 5.29 (s, 2H), 6.54 (s, 1H), 7.25–7.55 (m, 5H).

Example 6

Synthesis of

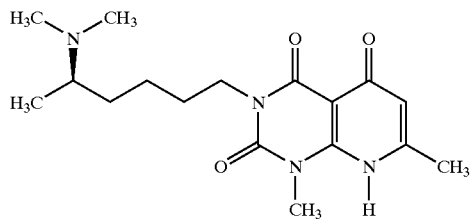

(R)-1,7-Dimethyl-3-(5-(N,N-dimethylamino)hexyl) pyrido[2,3-d]pyrimidine-2,4,5(1H,3H,8H)-trione, Acetic Acid Salt (CT-30271)

To a mixture of (R)-8-benzyl-1,7-dimethyl-3-(5-hydroxyhexyl)pyrido[2,3-d]pyrimidine-2,4,5(1H,3H,8H)-trione (1.26 g, 3.18 mmol), triphenylphosphine (2.50 g, 9.52 mmol), acetic acid (0.54 ml, 9.52 mmol) and tetrahydrofuran (20 ml), cooled in an ice bath, was added diethylazodicarboxylate (1.5 ml, 9.5 mmol) dropwise. After stirring at room temperature for 4hours, the mixture was concentrated under reduced pressure. The residue was purified by column chromatography on silica gel eluting with 20% ethyl acetate-hexanes to afford (S)-3-(5-acetoxyhexyl)-8-benzyl-1,7-dimethylpyrido[2,3-d]pyrimidine-2,4,5(1H,3H,8H)-trione (1.2 g, 86% yield) as an oil. $^1$H NMR (300 MHz, CDCl$_3$) δ 1.20 (d, 3H), 1.30–1.75 (m, 6H), 2.02 (s, 3H), 2.49 (s, 3H), 3.67 (s, 3H), 4.03 (t, 2H), 4.88 (sextet, 1H), 5.30 (s, 2H), 6.56 (s, 1H), 7.30–7.56 (m, 5H).

A mixture of (S)-3-(5-acetoxyhexyl)-8-benzyl-1,7-dimethylpyrido[2,3-d]pyrimidine-2,4,5(1H,3H,8H)-trione (1.2 g, 2.7 mmol), methanol (10 ml) and 37% aqueous hydrochloric acid (2 ml) was stirred at room temperature for 18 hours. The mixture was treated with saturated aqueous sodium bicarbonate solution (20 ml). The solid was filtered, rinsed with water, and air dried to afford (S)-8-benzyl-1,7-dimethyl-3-(5-hydroxyhexyl)pyrido[2,3-d]pyrimidine-2,4,5 (1H,3H,8H)-trione (850 mg, 89% yield) as a white fluffy powder. $^1$H NMR (300 MHz, CDCl$_3$) δ 1.17 (d, 3H), 1.38–1.6 (m, 6H), 2.47 (s, 3H), 3.63 (s, 3H), 3.78 (m, 1H), 4.05 (t, 2H), 5.28 (s, 2H), 6.56 (s, 1H), 7.23–7.57 (m, 5H).

A mixture of (S)-8-benzyl-1,7-dimethyl-3-(5-hydroxyhexyl)pyrido[2,3-d]pyrimidine-2,4,5(1H,3H,8H)-trione (356 mg, 0.90 mmol, 1.0 eq), methanesulfonic anhydride (234 mg, 1.34 mmol), dichloromethane (10 ml), and 4-dimethylaminopyridine (220 mg, 1.79 mmol) was stirred at room temperature for 2 hours. After concentration under reduced pressure, the residue was partitioned between ethyl acetate (50 ml) and 0.1 M aqueous hydrochloric acid (50 ml). The organic phase was dried over sodium sulfate and concentrated under vacuum to provide crude (S)-8-benzyl-1,7-dimethyl-3-(5-methanesulfonyloxyhexyl)pyrido[2,3-d] pyrimidine-2,4,5(1H,3H,8H)-trione as an oil which was used immediately in the next step.

A mixture of the crude (S)-8-benzyl-1,7-dimethyl-3-(5-methanesulfonyloxyhexyl)pyrido[2,3-d]pyrimidine-2,4,5 (1H,3H,8H)-trione, dimethylsulfoxide (6 ml) and sodium azide (116 mg, 1.79 mmol) was heated at 600 C for 18 hours. After cooling to room temperature, the mixture was partitioned between water (50 ml) and ethyl acetate (50 ml) and the aqueous layer was extracted with ethyl acetate (50 ml). The combined extracts were rinsed with water and with saturated aqueous sodium chloride solution. Concentrating under reduced pressure afforded (R)-3-(5-azidohexyl)-8-benzyl-1,7-dimethylpyrido[2,3-d]pyrimidine-2,4,5(1H,3H, 8H)-trione (380 mg, 99% yield for 2 steps) as an oil. $^1$H NMR (300 MHz, CDCl$_3$) δ 1.22 (d, 3H), 1.36–1.60)$_m$, 4H), 1.62–1.78 (m, 2H), 2.48 (s, 3H), 3.43 (m, 1H), 3.64 (s, 3H), 4.03 (t, 2H), 5.29 (s, 2H), 6.55 (s, 1H), 7.29

A mixture of (R)-3-(5-azidohexyl)-8-benzyl-1,7-dimethylpyrido[2,3-d]pyrimidine-2,4,5(1H,3H,8H)-trione (380 mg, 0.90 mmol), triphenylphosphine (260 mg, 0.99 mmol), water (0.1 ml) and tetrahydrofuran (15 ml) was stirred at room temperature for 18 hours followed by heating at 500 C for 4 hours. Another portion of triphenylphosphine (100 mg) was added and the mixture was heated at 65° C. for 18 hours. After concentration under reduced pressure, the residue was treated with 1.0 M aqueous hydrochloric acid (10 ml) and ethyl acetate (10 ml), followed by extraction of the organic layer with 1.0 M aqueous hydrochloric acid (2×10 ml). The combined aqueous layers were made slightly basic (pH~8) by addition of aqueous potassium hydroxide solution and extracted with ethyl acetate (2×20 ml). The combined organic extracts were dried over sodium sulfate and concentrated under reduced pressure to afford (R)-3-(5-aminohexyl)-8-benzyl-1,7-dimethylpyrido[2,3-d] pyrimidine-2,4,5(1H,3H,8H)-trione (155 mg, 43% yield) as a beige powder. $^1$H NMR (300 MHz, CDCl$_3$) δ 1.05 (d, 3H), 1.39 (broad s, 4H), 1.66 (m, 2H), 1.90 (broad s, 1H), 2.45 (s, 3H), 2.81 (broad s, 1H), 3.61 (s, 3H), 4.00 (t, 2H), 5.25 (s, 2H), 6.51 (s, 1H), 7.25–7.55 (m, 5H).

To a mixture of (R)-3-(5-aminohexyl)-8-benzyl-1,7-dimethylpyrido[2,3-d]pyrimidine-2,4,5(1H,3H,8H)-trione (155 mg, 0.391 mmol), methanol (20 ml), and 37% aqueous formaldehyde (3 ml) was added dropwise a solution of sodium cyanoborohydride (35 mg, 0.557 mmol) in methanol (1 ml). After stirring at room temperature for 4 hours, the mixture was concentrated under reduced pressure and partitioned between water (10 ml) and ethyl acetate (10 ml). The organic layer was dried over sodium sulfate and concentrated under reduced pressure. The residue was purified by column chromatography on silica gel eluting with ethyl acetate-methanol-triethylamine (38:1:1) to provide (R)-8-benzyl-1,7-dimethyl-3-(5-(N,N-dimethylamino)hexyl) pyrido[2,3-d]pyrimidine-2,4,5(1H,3H,8H)-trione (80 mg, 48% yield) as an oil. $^1$H NMR (300 MHz, CDCl$_3$) δ 0.96 (d, 3H), 1.25–1.75 (m, 6H), 2.21 2.49 (m, 1H), 2.50 (s, 3H), 3.67 (s, 3H), 4.04 (t, 2H), 5.30 (s, 2H), 6.55 (s, 1H), 7.30–7.56 (m, 5H).

A mixture of (R)-8-benzyl-1,7-dimethyl-3-(5-(N,N-dimethylamino)hexyl)pyrido[2,3-d]pyrimidine-2,4,5(1H, 3H,8H)-trione (80 mg), acetic acid (10 ml) and 10% Pd/C (20 mg) was treated with hydrogen gas (50 psi) on a Parr shaker for 18 hours. The mixture was filtered through a pad of celite and the solids were rinsed with acetic acid. The combined filtrates were concentrated under reduced pressure and then coevaporated with toluene (2×50 ml) to remove remaining acetic acid to provide (R)-1,7-dimethyl-3-(5-(N, N-dimethylamino)hexyl)pyrido[2,3-d]pyrimidine-2,4,5(1H, 3H,8H)-trione (74 mg, 99% yield) as a beige powder. $^1$H NMR (300 MHz, CDCl$_3$) δ 1.15 (d, 3H), 1.20–1.50 (m, 3H), 1.52–2.00 (m, 3H), 1.97 (s, 3H), 2.40 (s, 3H), 2.55(s, 6H), 3.15 (m, 1H), 3.58 (s, 3H), 3.97 (t, 2H), 6.40 (s, 1H), 9.50 (broad s, 1H).

Example 7

Synthesis of

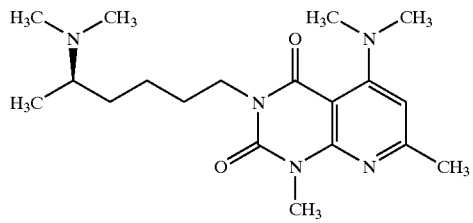

(R)-1,7-Dimethyl-5-(N,N-dimethylamino)-3-(5-(N, N-dimethylamino)hexyl)pyrido[2,3-d]pyrimidine-2,4 (1H,3H)dione (CT-31818)

To a mixture of (R)-1,7-dimethyl-3-(5-(N,N-dimethylamino)hexyl)pyrido[2,3-d]pyrimidine-2,4,5(1H, 3H,8H)-trione (315 mg, 0.947 mmol), pyridine (1 ml, 12.4 mmol) and dichloromethane (20 ml), cooled in an ice bath, was added trifluoromethanesulfonic anhydride (0.315 ml, 1.87 mmol) dropwise. After stirring for 2 hours, the cooling bath was removed. A 30% (v:v) solution of dimethylamine in tetrahydrofuran (7 ml) was added and the solution was transferred to a pressure tube (1"×8"). The tube was sealed and heated to 55° C. for 2 hours. After cooling to room temperature the solution was concentrated under reduced pressure. The residue was dissolved in ethyl acetate and the solution filtered through a pad of celite. The filtrate was rinsed with saturated sodium bicarbonate solution, dried over sodium sulfate, and concentrated under reduced pressure. The residue was purified by column chromatography on silica gel eluting with ethyl acetate-methanol-triethylamine (85:10:5) to afford (R)-1,7-Dimethyl-5-(N,N-dimethylamino)-3-(5-(N,N-dimethylamino)hexyl)pyrido[2, 3-d]pyrimidine-2,4(1H,3H)dione (300 mg, 88% yield for 2 steps) as an oil. $^1$H NMR (300 MHz, CDCl$_3$) δ 0.99 (d, 3H), 1.20–1.50 (m, 3H), 1.52–1.74 (m, 3H), 2.28 (s, 6H), 2.42 (s, 3H), 2.99 (s, 6H), 3.64 (s, 3H), 4.03 (t, 2H), 6.39 (s, 1H).

Example 8

Synthesis of

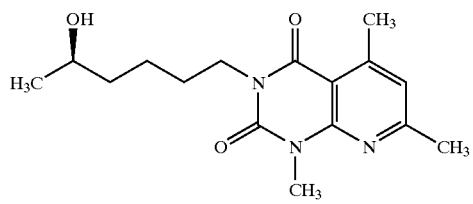

(R)-3-(5-Hydroxyhexyl)-1,5,7-trimethylpyrido[2,3-d]pyrimidine-2,4(1H,3H)-dione (CT-30144)

A mixture of (R)-3-(5-acetoxyhexyl)-6-amino-1-methyluracil (250 mg, 0.88 mmol), 2,4-pentanedione (2 ml, 19.5 mmol) and xylenes (3 ml) was heated to 145° C. for 18 hours. The mixture was concentrated under reduced pressure followed by coevaporation with toluene (2×5 ml) to remove the remaining 2,4-pentanedione to provide crude (R)-3-(5-acetoxyhexyl)-1,5,7-trimethylpyrido[2,3-d]pyrimidine-2,4 (1H,3H)-dione.

To a solution of the crude (R)-3-(5-acetoxyhexyl)-1,5,7-trimethylpyrido[2,3-d]pyrimidine-2,4(1H,3H)-dione in methanol (10 ml) and was added a solution of potassium hydroxide (200 mg) in water (1 ml) was added. After stirring at room temperature for 3 hours, saturated aqueous sodium chloride solution (5 ml) and water (5 ml) were added. The methanol was evaporated under reduced pressure and the aqueous mixture was extracted with ethyl acetate (20 ml). The organic layer was applied to a short column of silica gel. Elution with ethyl acetate afforded (R)-3-(5-hydroxyhexyl)-1,5,7-trimethylpyrido[2,3-d]pyrimidine-2,4(1H,3H)-dione (227 mg, 84% yield) as an oil. $^1$H NMR (300 MHz, CDCl$_3$) δ 1.19 (d, 3H), 1.33–1.79 (m, 6H), 2.53 (s, 3H), 2.77 (s, 3H), 3.68 (s, 3H), 3.80 (m, 1H), 4.04 (t, 2H), 6.82 (s, 1H).

Example 9

Synthesis of

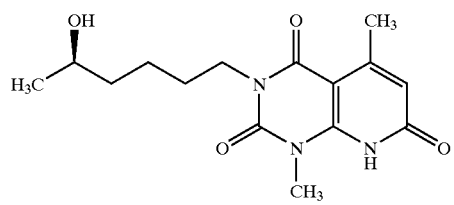

(R)-1,5-Dimethyl 3-(5-hydroxyhexyl)pyrido[2,3-d] pyrimidine-2,4,7(1H,3H,8H)-trione (CT-30001)

A solution of (R)-3-(5-acetoxyhexyl)-6-amino-1-methyluracil (3.0 g, 10.6 mmol), diketene (1.2 ml, 15.9 mmol), hydroquinone (50 mg, 0.45 mmol) and dichloroethane (100 ml) was heated at reflux for 36 hours. After cooling to room temperature, the solution was washed with water, dried over sodium sulfate, and concentrated under vacuum. The residue was purified by column chromatography on silica gel eluting with 20% ethyl acetate-toluene followed by 50% ethyl acetate-toluene) to provide (R)-3-(5-acetoxyhexyl)-1,7-dimethylpyrido[2,3-d]pyrimidine-2,4, 5(1H,3H,8H)-trione (1.45 g, 39% yield) followed by (R)-3-(5-acetoxyhexyl)-1,5-dimethylpyrido[2,3-d]pyrimidine-2,4, 7(1H,3H,8H)-trione (1.26 g, 34% yield). $^1$H NMR (300 MHz, CDCl$_3$) δ 1.17 (d, 3H), 1.28–1.67 (m, 6H), 1.99 (s, 3H), 2.67 (s, 3H), 3.59 (s, 3H), 3.95 (t, 2H), 4.85 (sextet, 1H), 6.23 (s, 1H). $^{13}$C NMR (75 MHz, CDCl$_3$) δ 19.65, 21.16, 22.58, 22.74, 27.31, 29.87, 35.25, 41.34, 70.88, 100.16, 109.56, 150.05, 150.49, 156.07, 160.41, 164.03, 171.07.

A mixture of (R)-3-(5-acetoxyhexyl)-1,5-dimethylpyrido [2,3-d]pyrimidine-2,4,7(1H,3H,8H)-trione (175 mg, 0.50 mmol), methanol (5 ml) and 12 M aqueous hydrochloric acid (1 ml) was stirred at room temperature for 18 hours and then treated with saturated aqueous sodium bicarbonate solution (10 ml). After concentrating under reduced pressure to remove the methanol, the aqueous mixture was extracted with ethyl acetate (20 ml). The extract was applied to a short column of silica gel and eluted with ethyl acetate to afford (R)-1,5-dimethyl-3-(5-hydroxyhexyl)pyrido[2,3-d] pyrimidine-2,4,7(1H,3H,8H)-trione (50 mg, 32% yield) as a white powder. $^1$H NMR (300 MHz, CDCl$_3$) δ 1.17 (d, 3H), 1.30–1.71 (m, 6H), 2.67 (s, 3H), 3.57 (s, 3H), 3.72–3.88 (m, 1H), 3.98 (t, 2H), 6.23 (s, 1H).

Example 10

Synthesis of

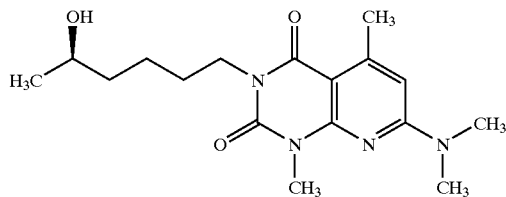

(R)-1,5-Dimethyl-7-(N,N-dimethylamino)-3-(5-hydroxyhexyl)-2,4-pyrido[2,3-d]pyrimidine-2,4(1H,3H)-dione (CT-30113)

To a mixture of (R)-3-(5-acetoxyhexyl)-1,5-dimethylpyrido[2,3-d]pyrimidine-2,4,7(1H,3H,8H)-trione (440 mg, 1.259 mmol), dichloromethane (10 ml), pyridine (0.5 ml, 6.29 mmol), cooled in an ice bath, was added trifluoromethanesulfonic anhydride (0.42 ml, 2.52 mmol) dropwise. After stirring for 1 hour, the cooling bath was removed and the solution was concentrated under reduced pressure. The residue was purified by short column chromatography on silica gel eluting with ethyl acetate to afford (R)-3-(5-acetoxyhexyl)-1,5-dimethyl-7-trifluoromethanesulfonyloxypyrido[2,3-d]pyrimidine-2,4(1H,3H)-dione 405 mg, 67% yield) as an orange powder. $^1$H NMR (300 MHz, CDCl$_3$) δ 1.20 (d, 3H), 1.30–1.75 (m, 6H), 2.02 (s, 3H), 2.87 (s, 3H), 3.62 (s, 3H), 4.02 (t, 2H), 4.89 (sextet, 1H), 6.78 (s, 1H).

A 60 ml pressure tube was charged with tetrahydrofuran (1 ml) and cooled an ice bath. Dimethylamine gas was introduced until 1 ml had been condensed. (R)-3-(5-Acetoxyhexyl)-1,5-dimethyl-7-trifluoromethanesulfonyloxypyrido[2,3-d]pyrimidine-2,4(1H,3H)-dione (110 mg, 0.23 mmol) was added, the tube sealed, and the mixture was heated to 60° C. for 1 hour. After cooling to room temperature, the tube was vented and remaining dimethylamine was evaporated. Methanol (4 ml) was added followed by a solution of potassium hydroxide (100 mg) in water (1 ml). The mixture was stirred at room temperature for 12 hours. After treating with saturated aqueous ammonium chloride solution (10 ml), the mixture was concentrated under reduced pressure to remove organic solvents. The aqueous mixture was extracted with ethyl acetate (20 ml). The organic layer was washed with saturated aqueous sodium chloride solution, with water, and concentrated under reduced pressure to provide (R)-1,5-Dimethyl-7-(N,N-dimethylamino)-3-(5-hydroxyhexyl)-2,4-pyrido[2,3-d]pyrimidine-2,4(1H,3H)-dione (75 mg, 98% yield for 2 steps) as a beige powder. $^1$H NMR (300 MHz, benzene d$_6$) δ1.02 (d, 3H), 1.25–1.51 (m, 4H), 1.75–1.92 (m, 2H), 2.47 (s, 6H), 2.80 (s, 3H), 3.47 (s, 3H), 3.50–3.60 (m, 1H), 4.21 (t, 2H), 5.66 (s, 1H).

Example 11

Effect on IL-12 Signaling

This example illustrates the inventive compounds' ability to suppress Th1 differentiation in vitro by blocking IL-12 signaling. The compounds from Examples 1, 2, 6, and 7 were tested in an IL-12 dependent in vitro T-helper cell differentiation assay as described in LeGross et al., J. Exp. Med., 172:921–929 (1990). Recombinant IL-12 was used to induce Th1 differentiation. Splenic T cells were purified utilizing the antibodies RA3-3A1/6.1 (anti-B220), J11d and MAR18.5 (anti-rat kappa chain) to deplete the B cells by magnetic bead separation, as described in Coon et al, *J. Immuno.*, 163:6567–6574 (1989). Splenic T cells were stimulated at 5×105/ml with insoluble anti-CD3 alone (145-2C11, Pharmingen, San Diego, Calif.), or anti-CD3 and 5 U/ml IL-12, with and without each inventive compound. After seven days, equal numbers of viable cells were restimulated for 24 hours with anti-CD3 without the inventive compounds, and the supernatants were collected and assayed for IFN—γ production. IFN-γ and IL-4 levels were measured by ELISA test specific for IFN-γ and IL-4. The results are shown in Table 1 below.

Th1 differentiation was induced by culturing anti-CD3 stimulated T cells in the presence of exogenous IL-12. Under these conditions, Th1 differentiation was consistently enhanced as compared to T cells stimulated with anti-CD3 alone. It was observed that the presence of the tested compounds during T cell activation inhibited Th1 differentiation, which had been enhanced by the addition of exogenous IL-12. The values in the "IC50 μM" column were determined by measuring the inhibition of IL-12 induced Th1 differentiation as defined by IFN-γ production upon secondary stimulation with anti-CD3 alone. None of the compounds affected the viability or recovery of T cells after one week of culture.

TABLE 1

| Ex. | STRUCTURE | CT NO. | IC50 μM |
|---|---|---|---|
| 1 | (structure shown) | CT-12480 | 19 |
|   |   |   | 24 |
|   |   |   | 28 |

TABLE 1-continued

| Ex. | STRUCTURE | CT NO. | IC50 μM |
|---|---|---|---|
| 2 | [structure: 3-(4-methoxypentyl)-1,7-dimethyl-pyrido[2,3-d]pyrimidine-2,4,5-trione] | CT-13415 | 7 |
| 6 | [structure: 3-(4-dimethylamino-pentyl)-1,7-dimethyl-pyrido[2,3-d]pyrimidine-2,4,5-trione] | CT-30271 | 14<br>16 |
| 7 | [structure: 3-(4-dimethylaminopentyl)-5-(dimethylamino)-1,7-dimethyl-pyrido[2,3-d]pyrimidine-2,4-dione] | CT-31818 | >40 |

Example 11

Effect on IL-4 Signaling

The compounds of Examples 1, 2, 6 and 7 were tested to determine their ability to block the differentiation of T0 cells to T2 effectors as judged by their relative inability to secrete the canonical T2 effector cytokine, IL-4, following treatment with the compounds. In a series of experiments analogous to the T1 differentiation assay of Example 10 (in which T0 cells were induced to become T1 effectors by polyclonal stimulation in the presence of IL-12), the above compounds were effective in a T2 differentiation assay in which T0 cells are stimulated in the presence of IL-4, which affects T2 differentiation. The resulting effector cells were observed as being deficient in IL-4 production, though they showed signs of activation and they proliferated normally. The results are shown in Table 2 below.

TABLE 2

| Ex. | STRUCTURE | CT NO. | Th2 |
|---|---|---|---|
| 1 | [structure: 3-(4-hydroxypentyl)-1,7-dimethyl-pyrido[2,3-d]pyrimidine-2,4,5-trione] | CT-12480 | 11 |
| 2 | [structure: 3-(4-methoxypentyl)-1,7-dimethyl-pyrido[2,3-d]pyrimidine-2,4,5-trione] | CT-13415 | >40 |

TABLE 2-continued

| Ex. | STRUCTURE | CT NO. | Th2 |
|---|---|---|---|
| 6 | [structure] | CT-30271 | >40 |
| 7 | [structure] | CT-31818 | 29<br>8.5 |

Example 12

Modified Acute Assay

The compounds of Examples 3–10 were tested in a modified acute assay which is used to screen for compounds that perturb IL-12 signaling. The assay measures the biological effects of compounds on IL-12 signaling during the differentiation of T1 responses rather than the outcome of differentiation, as measured using a T1 Differentiation Assay. Purified splenic T cells were stimulated either by crosslinking their T cell receptors with immobilized anti-CD3 antibody or by binding with a soluble lectin (e.g. Conconavalin A). The cells were incubated for 72 hours after which time supernatants are collected and relative Interferon-γ amounts determined by ELISA. The Modified Acute Assay measured a directed IL-12 response derived from a population of cells in a variety of activation states and can be thought of as a more stochastic response. The results are shown in Table 3 below.

TABLE 3

| Ex. | STRUCTURE | CT NO. | Acute |
|---|---|---|---|
| 3 | [structure] | CT-30102 | <10 |
| 4 | [structure] | CT-30103 | 8<br>>40 |

TABLE 3-continued

| Ex. | STRUCTURE | CT NO. | Acute |
|---|---|---|---|
| 5 | 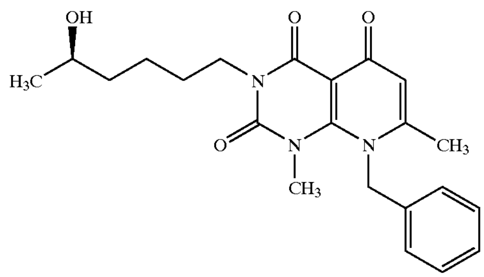 | CT-30059 | 8 |
| 6 | 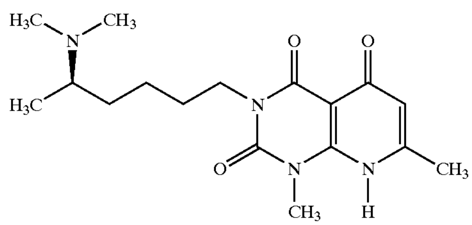 | CT-30271 | 9, 8 |
| 7 | 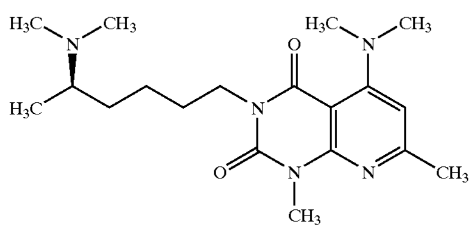 | CT-31818 | 26, 34 |
| 8 | 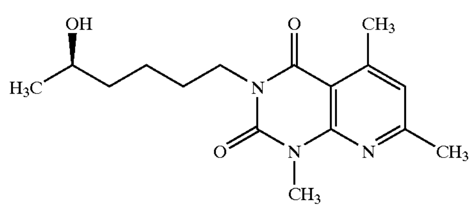 | CT-30144 | 33 |
| 9 | 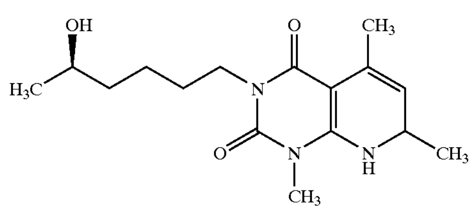 | CT-30001 | >40 |
| 10 | 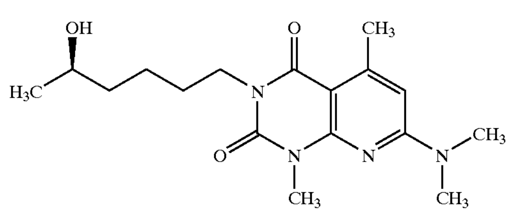 | CT-30113 | 6 |

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A therapeutic compound, including resolved enantiomers, diastereomers, tautomers, and salts thereof, having the following formula:

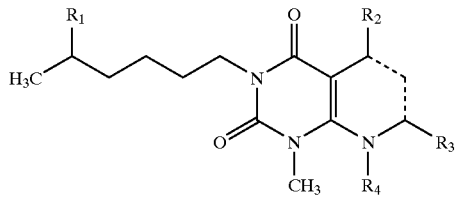

wherein:

$R_1$ is selected from a member of the group consisting of hydrogen, hydroxyl, methoxyl, acylamino group, cyano group, sulfo; sulfinyl, sulfhydryl (mercapto), sulfeno, sulfanilyl, sulfamyl, sulfamino, and phosphino, phosphinyl, phospho, phosphono and —$NR_aR_b$, wherein each of $R_a$ and $R_b$ may be the same or different and each is selected from the group consisting of hydrogen and optionally substituted: $C_{(1-20)}$ alkyl, $C_{(3-12)}$cycloalkyl, $C_{(2-20)}$alkenyl, $C_{(3-12)}$ cycloalkenyl, $C_{(2-20)}$alkynyl, aryl, heteroaryl, and heterocyclic group;

$R_2$ and $R_3$ are independently selected from a member of the group consisting of halo, oxo, $C_{(1-20)}$alkyl, $C_{(1-20)}$ hydroxyalkyl, $C_{(1-20)}$alkylthio, $C_{(1-20)}$alkylaminoalkyl, $C_{(1-20)}$aminoalkyl, $C_{(1-20)}$aminoalkoxyalkenyl, $C_{(1-20)}$ aminoalkoxyalkynyl, $C_{(1-20)}$diaminoalkyl, $C_{(1-20)}$ triaminoalkyl, $C_{(2-20)}$tetraaminoalkyl, $C_{(1-20)}$ alkylamido, $C_{(1-20)}$alkylamidoalkyl, $C_{(1-20)}$amidoalkyl, $C_{(1-20)}$acetamidoalkyl, $C_{(2-20)}$alkenyl, $C_{(2-20)}$alkynyl, $C_{(1-20)}$alkoxyl, $C_{(1-20)}$alkoxyalkyl, $C_{(1-20)}$ dialkoxyalkyl, and –$NR_aR_b$; and $R_4$ may be hydrogen or an optionally substituted member of the group consisting of $C_{(1-20)}$alkyl, $C_{(3-12)}$ cycloalkyl, $C_{(2-20)}$alkenyl, $C_{(3-12)}$cycloalkenyl, $C_{(2-20)}$ alkynyl, aryl, heteroaryl, and heterocyclic group.

2. The therapeutic compound of claim 1, wherein $R_2$ and $R_3$ are independently selected from a member of the group consisting of hydrogen, halo, thio, oxo, $C_{(1-10)}$alkyl, $C_{(1-10)}$ hydroxyalkyl, $C_{(1-10)}$alkylthio, $C_{(1-10)}$alkylamino, $C_{(1-10)}$ alkylaminoalkyl, $C_{(1-10)}$aminoalkyl, $C_{(1-10)}$ aminoalkoxyalkenyl, $C_{(1-10)}$aminoalkoxyalkynyl, $C_{(1-10)}$ diaminoalkyl, $C_{(1-10)}$triaminoalkyl, $C_{(2-10)}$tetraaminoalkyl, $C_{(1-10)}$aminotrialkoxyamino, $C_{(1-10)}$alkylamido, $C_{(1-10)}$ alkylamidoalkyl, $C_{(1-10)}$amidoalkyl, $C_{(1-10)}$acetamidoalkyl, $C_{(2-10)}$alkenyl, $C_{(2-10)}$alkynyl, $C_{(1-10)}$)alkoxyl, $C_{(1-10)}$ alkoxyalkyl, and $C_{(1-10)}$dialkoxyalkyl.

3. A therapeutic compound, including resolved enantiomers, diastereomers, tautomers, and salts thereof, having the formula:

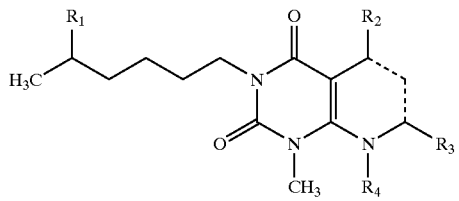

wherein:

$R_1$ is selected from a member of the group consisting of hydrogen, hydroxyl, methoxyl, acylamino group, cyano group, sulfo, sulfonyl, sulfinyl, sulfhydryl (mercapto), sulfeno, sulfanilyl, sulfamyl, sulfamino, phosphino, phosphinyl, phospho, phosphono and —$NR_aR_b$, wherein each of $R_a$ and $R_b$ may be the same or different and each is selected from the group consisting of hydrogen and optionally substituted: $C_{(1-20)}$ alkyl, $C_{(3-12)}$cycloalkyl, $C_{(2-20)}$alkenyl, $C_{(3-12)}$ cycloalkenyl, $C_{(2-20)}$alkynyl, aryl, heteroaryl, and heterocyclic group;

$R_2$ and $R_3$ are independently selected from a unsubstituted or substituted member of the group consisting of methyl, ethyl, oxo, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, methylamino, amino-methyl, and methylphenyl; and $R_4$ may be hydrogen or an optionally substituted member of the group consisting of $C_{(1-20)}$alkyl, $C_{(3-12)}$ cycloalkyl, $C_{(2-20)}$alkenyl, $C_{(3-12)}$cycloalkenyl, $C_{(2-20)}$ alkynyl, aryl, heteroaryl, and heterocyclic group.

4. The therapeutic compound of claim 3, wherein each of $R_2$ and $R_3$ is substituted with one or more members of the group consisting of hydroxyl, methyl, carboxyl, furyl, furfuryl, biotinyl, phenyl, naphthyl, amino group, amido group, carbamoyl group, cyano group, sulfo, sulfonyl, sulfinyl, sulfhydryl, sulfeno, sulfanilyl, sulfamyl, sulfamino, phosphino, phosphinyl, phospho, phosphono, N—OH, —Si $(CH_3)_3$, $C_{(1-3)}$alkyl, $C_{(1-3)}$hydroxyalkyl, $C_{(1-3)}$alkylamino, benzyldihydrocinnamoyl group, benzoyldihydrocinnamido group, optionally substituted heterocyclic group and optionally substituted carbocyclic group.

5. The therapeutic compound of claim 4, wherein the heterocyclic group or carbocyclic group is substituted with one or more members of the group consisting of halo, hydroxyl, nitro, $SO_2NH_2$, $C_{(1-6)}$alkyl, $C_{(1-6)}$haloalkyl, $C_{(1-6)}$ alkoxyl, $C_{(1-11)}$alkoxyalkyl, $C_{(1-6)}$alkylamino, and $C_{(1-6)}$ aminoalkyl.

6. The therapeutic compound of claim 4, wherein the heterocyclic group is a member selected from the group consisting of acridinyl, aziridinyl, azocinyl, azepinyl, benzimidazolyl, benzodioxolanyl, benzofuranyl, benzothiophenyl, carbazole, 4a H-carbazole, chromanyl, chromenyl, cinnolinyl, decahydroquinolinyl, dioxoindolyl, furazanyl, furyl, furfuryl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthyridinyl, octahydroisoquinolinyl, oxazolidinyl, oxazolyl, oxiranyl, perimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, 4-pipendonyl, piperidyl, pteridinyl, purinyl, pyranyl, pyrazinyl, pyrazolidinyl, pyrazolinyl, pyrazolyl, pyridazinyl, pyndinyl, pyridyl, pyndyl, pyrimidinyl, pyrrolidinyl, 2-pyrrolidonyl, pyrrolonyl, pyrrolyl, 2H-pyrrolyl, quinazolinyl, 4H-quinolizinyl, quinolinyl, quinoxalinyl, quinuclidinyl, β-carbolinyl, tetrahydrofuranyl, tetrahydroisoquinolinyl, tetrahydroquinolinyl, tetrazolyl, 6H- 1,2,5-thiadiazinyl, 2H-, 6H- 1,5,2-dirhiazinyl, thianthrenyl, thiazolyl, thienyl, thiophenyl, triazinyl, xanthenyl and xanthinyl.

7. The therapeutic compound of claim 4, wherein the carbocyclic group is a member selected from the group consisting of adamantyl, anthracenyl, benzyl, bicyclo[2.2.1]heptanyl, bicyclo[2.2.1]hexanyl, bicyclo[2.2.2]octanyl, bicyclo[3.2.0]heptanyl, bicyclo[4.3.0]-nonanyl, bicyclo[4.4.0]decanyl, biphenyl, biscyclooctyl, cyclobutyl, cyclobutenyl, cycloheptyl, cycloheptenyl, cyclohexanedionyl, cyclohexenyl, cyclohexyl, cyclooctanyl, cyclopentadienyl, cyclopentanedionyl, cyclopentenyl, cyclopentyl, cyclopropyl, decalinyl, 1,2-diphenylethanyl, indanyl, 1-indanonyl, indenyl, naphthyl, napthlalenyl, phenyl, resorcinolyl, stilbenyl, tetrahydronaphthyl, tetralinyl, tetralonyl, and tricyclododecanyl.

8. A compound, including resolved enantiomers, diastereomers, tautomers, and salts thereof, having the formula:

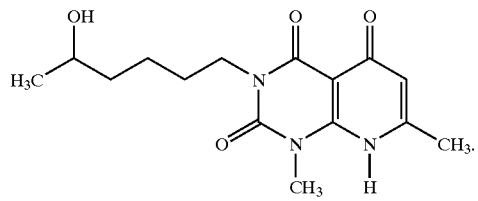

9. A compound, including resolved enantiomers, diastereomers, tautomers, and salts thereof, having the formula:

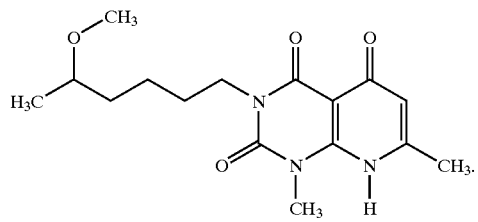

10. A compound, including resolved enantiomers, diastereomers, tautomers, and salts thereof, having the formula:

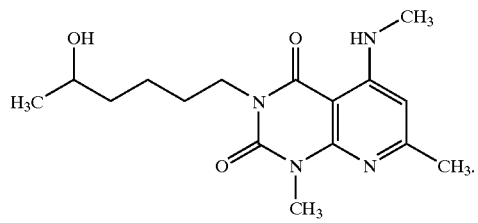

11. A compound, including resolved enantiomers, diastereomers, tautomers, and salts thereof, having the formula:

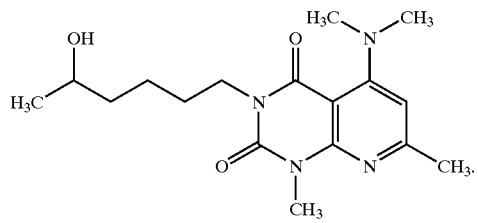

12. A compound, including resolved enantiomers, diastereomers, tautomers, and salts thereof, having the formula:

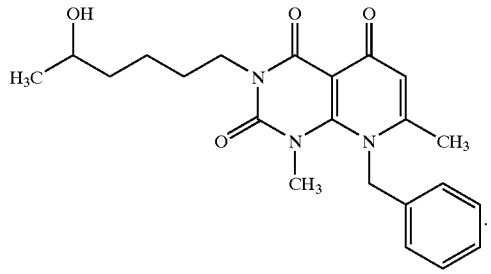

13. A compound, including resolved enantiomers, diastereomers, tautomers, and salts thereof, having the formula:

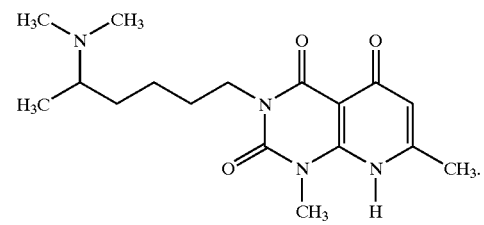

14. A compound, including resolved enantiomers, diastereomers, tautomers, and salts thereof, having the formula:

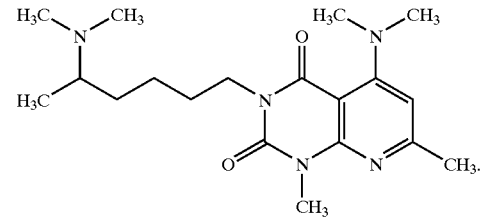

15. A compound, including resolved enantiomers, diastereomers, tautomers, and salts thereof, having the formula:

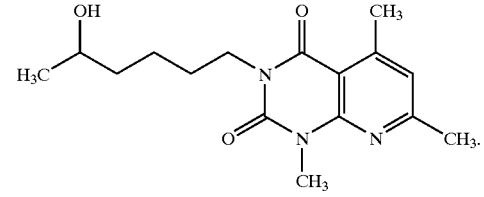

16. A compound, including resolved enantiomers, diastereomers, tautomers, and salts thereof, having the formula:

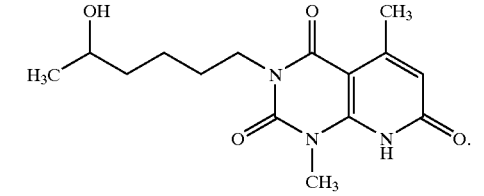

17. A compound, including resolved enantiomers, diastereomers, tautomers, and salts thereof, having the formula:

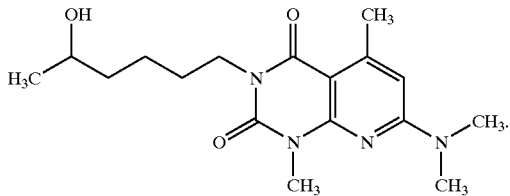

18. A pharmaceutical composition comprising the compound of claim 1 in admixture with a pharmaceutically acceptable carrier, adjuvant or vehicle.

19. A method for treating a T1 cell-mediated inflammatory response in a mammal in need of such treatment, the method comprising administering to the mammal a therapeutically effective amount of the compound of claim 1.

20. The method of claim 19, wherein the inflammatory response is associated with a disease or condition selected from the group consisting of chronic inflammatory disease, chronic intestinal inflammation, arthritis, psoriasis, asthma and autoimmune disorders.

21. The method of claim 19, wherein said autoimmune disorder is selected from Type-1 IDDM, multiple sclerosis, rheumatoid arthritis, uveitis, inflammatory bowel disease, lupus disorders, and acute and chronic graft-versus-host disease.

22. The method of claim 19, wherein said mammal is a human.

23. A method for treating a T2 cell-mediated anti-inflammatory response in a mammal in need of such treatment, the method comprising administering to the mammal a therapeutically effective amount of the compound of claim 1.

24. The method of claim 23, wherein the anti-inflammatory response is associated with a disease or condition selected from the group consisting of asthma, atopic dermatitis, hay fever, eczema, urticaria and food allergy.

25. The method of claim 24, wherein said disease is asthma.

26. The method of claim 23, wherein said mammal is a human.

27. A method for treating NIDDM comprising a step of administering to a subject in need of such treatment a therapeutically effective amount of the compound of claim 1.

* * * * *